(12) United States Patent
Nukui et al.

(10) Patent No.: US 9,078,926 B2
(45) Date of Patent: Jul. 14, 2015

(54) POLYMER CONJUGATES WITH A LINKER

(71) Applicant: NITTO DENKO CORPORATION, Osaka (JP)

(72) Inventors: Seiji Nukui, San Diego, CA (US); Kwok Yin Tsang, Irvine, CA (US); Chunfeng Yin, San Diego, CA (US); Yi Jin, Carlsbad, CA (US); Lei Yu, Carlsbad, CA (US)

(73) Assignee: Nitto Denko Corporation, Ibaraki, Osaka (JP)

( * ) Notice: Subject to any disclaimer, the term of this patent is extended or adjusted under 35 U.S.C. 154(b) by 195 days.

(21) Appl. No.: 13/791,137

(22) Filed: Mar. 8, 2013

(65) Prior Publication Data

US 2013/0295039 A1    Nov. 7, 2013

Related U.S. Application Data

(60) Provisional application No. 61/643,793, filed on May 7, 2012.

(51) Int. Cl.
```
A61K 31/045    (2006.01)
A61K 31/337    (2006.01)
A61K 31/40     (2006.01)
A61K 38/02     (2006.01)
A61K 47/34     (2006.01)
A61K 47/48     (2006.01)
```
(52) U.S. Cl.
CPC ..... *A61K 47/48207* (2013.01); *A61K 47/48315* (2013.01)

(58) Field of Classification Search
CPC ... A61K 31/05; A61K 31/045; A61K 31/337; A61K 47/34; A61K 47/48; A61K 47/48207
USPC .......... 514/772.1, 449, 283; 424/78.17, 78.37
See application file for complete search history.

(56) References Cited

U.S. PATENT DOCUMENTS

| | | | |
|---|---|---|---|
| 3,350,365 | A | 10/1967 | Wakasa et al. |
| 4,892,733 | A | 1/1990 | Bichon et al. |
| 2007/0128118 | A1 | 6/2007 | Yu et al. |
| 2008/0181852 | A1 | 7/2008 | Yu et al. |
| 2008/0253969 | A1 | 10/2008 | Yu et al. |
| 2008/0277652 | A1 | 11/2008 | Mochizuki et al. |
| 2008/0279777 | A1 | 11/2008 | Van et al. |
| 2008/0279778 | A1 | 11/2008 | Van et al. |
| 2008/0279782 | A1 | 11/2008 | Van et al. |
| 2009/0226393 | A1 | 9/2009 | Wang et al. |
| 2010/0028416 | A1 | 2/2010 | Yu et al. |
| 2010/0034837 | A1 | 2/2010 | Beria et al. |
| 2010/0048490 | A1* | 2/2010 | Vlahov et al. .................. 514/16 |
| 2010/0093935 | A1 | 4/2010 | Van et al. |
| 2011/0144315 | A1 | 6/2011 | Wang et al. |
| 2011/0224148 | A1 | 9/2011 | Ahmadian et al. |
| 2012/0052015 | A1 | 3/2012 | Yu et al. |
| 2013/0272993 | A1 | 10/2013 | Tsang et al. |

OTHER PUBLICATIONS

International Preliminary Report on Patentability dated Nov. 11, 2014 for PCT Application No. PCT/US2013/030038, filed Mar. 8, 2013.
Bourke, et al., "Polymers derived from the amino acid L-tyrosine: polycarbonates, polyarylates and copolymers with poly(ethylene glycol)," *Adv. Drug Del. Rev.*, (2003) 55:447-466.
Constantinides, et al., "Formulation Development and Antitumor Activity of a Filter-Sterilizable Emulsion of Paclitaxel," *Pharmaceutical Research*, (2000) 17(2):175-182.
Damascelli, et al., "Intraarterial chemotherapy with polyoxyethylated castor oil free paclitaxel, incorporated in albumin nanoparticles (ABI-007): Phase I study of patients with squamous cell carcinoma of the head and neck and anal canal: preliminary evidence of clinical activity," *Cancer*, (2001) 92(10):2592-2602.
Duncan, Ruth, "The Dawning era of polymer therapeutics," *Nature Reviews Drug Discovery*, (2003) 2:347-360.
Greene, et al., "Protective Groups in Organic Synthesis," 3rd Ed., John Wiley & Sons, New York, NY, (1999) [Table of Contents Only].
Heller, et al., "Poly(ortho esters): synthesis, characterization, properties and uses," *Adv. Drug Del. Rev.*, (2002) 54:1015-1039.
Ibrahim, et al., "Phase I and pharmacokinetic study of ABI-007, a Cremophor-free, protein-stabilized, nanoparticle formulation of paclitaxel," *Clin. Cancer Res.*, (2002) 8:1038-1044.
Kumar, et al., "Polyanhydrides: an overview," *Adv. Drug Del. Rev.*, (2002) 54:889-910.
Panyam, et al., "Biodegradable nanoparticles for drug and gene delivery to cells and tissue." *Adv. Drug Deliv. Rev.*, (2003) 55:329-347.
Remington, *Remington's Pharmaceutical Sciences*, 18th Ed., Mack Publishing Co., Easton, PA (1990) [Table of Contents Only].
Sparreboom, et al., "Cremophor EL-mediated Alteration of Paclitaxel Distribution in Human Blood: Clinical Pharmacokinetic Implications," *Cancer Research*, (1999) 59:1454-1457.
Uhrich, et al., "Polymeric Systems for Controlled Drug Release," *Chem. Rev.*, (1999) 99:3181-3198.
Van, S. et al., Synthesis, characterization, and biological evaluation of poly(L-gamma-glutamyl-glutamine)-paclitaxel nanoconjugate, International Journal of Nanomedicine, 2010, vol. 5, pp. 825-837.
Wani, et al., "Plant antitumor agents. VI. The isolation and structure of taxol, a novel antileukemic and antitumor agent from *Taxus brevifolia*," *J. Am. Chem. Soc.*, (1971) 93(9):2325-2327.
International Search Report and Written Opinion dated May 27, 2013 in PCT Application No. PCT/US2013/030038, filed on Mar. 8, 2013.

* cited by examiner

*Primary Examiner* — Richard Schnizer
*Assistant Examiner* — Alma Pipic
(74) *Attorney, Agent, or Firm* — Knobbe Martens Olson & Bear LLP

(57) ABSTRACT

This application relates generally to biocompatible water-soluble polymers with pendant functional groups and methods for making them, and particularly to polyglutamate amino acid conjugates that can include a linker to a compound that can include a drug, and their use for a variety of drug delivery applications, e.g., anticancer.

19 Claims, 6 Drawing Sheets

POLYMER CONJUGATES WITH A LINKER

INCORPORATION BY REFERENCE TO ANY PRIORITY APPLICATIONS

Any and all applications for which a foreign or domestic priority claim is identified in the Application Data Sheet as filed with the present application, are hereby incorporated by reference under 37 CFR 1.57, and include U.S. provisional application No. 61/643,793, filed May 7, 2012.

BACKGROUND

1. Field

This application relates generally to biocompatible water-soluble polymers with pendant functional groups and methods for making them, and particularly to polyglutamate amino acid conjugates that can include a linker to a compound that can include a drug, and their use for a variety of drug delivery applications, e.g., anticancer.

2. Description

A variety of systems have been used for the delivery of drugs. For example, such systems include capsules, liposomes, microparticles, nanoparticles, and polymers. Several polyester-based biodegradable systems have been characterized and studied. Polylactic acid (PLA), polyglycolic acid (PGA) and their copolymers polylactic-co-glycolic acid (PLGA) are some of the most well-characterized biomaterials with regard to design and performance for drug-delivery applications. See Uhrich, K. E.; et al., *Chem. Rev.* (1999) 99:3181-3198 and Panyam J. et al., *Adv Drug Deliv Rev.* (2003) 55:329-47. Biodegradable systems based on poly-orthoesters have also been investigated. See Heller, J. et al., *Adv. Drug Del. Rev.* (2002) 54:1015-1039. Additionally, polyanhydride systems have been investigated. Such polyanhydrides are typically biocompatible and may degrade in vivo into relatively non-toxic compounds that are eliminated from the body as metabolites. See Kumar, N. et al., *Adv. Drug Del. Rev.* (2002) 54:889-91.

Amino acid-based polymers have been considered as a potential source of new biomaterials. Poly-amino acids having good biocompatibility have been investigated to deliver low molecular-weight compounds. A relatively small number of polyglutamic acids and copolymers have been identified as candidate materials for drug delivery. See Bourke, S. L. et al., *Adv. Drug Del. Rev.* (2003) 55:447-466.

Administered hydrophobic anticancer drugs, therapeutic proteins and polypeptides often suffer from poor bio-availability. Such poor bio-availability may be due to incompatibility of bi-phasic solutions of hydrophobic drugs and aqueous solutions and/or rapid removal of these molecules from blood circulation by enzymatic degradation. One technique for increasing the efficacy of administered proteins and other small molecule agents entails conjugating the administered agent with a polymer, such as a polyethylene glycol ("PEG") molecule, that can provide protection from enzymatic degradation in vivo. Such "PEGylation" often improves the circulation time, and, hence, bio-availability of an administered agent.

PEG has shortcomings in certain respects, however. For example, because PEG is a linear polymer, the steric protection afforded by PEG is limited, as compared to branched polymers. Another shortcoming of PEG is that it is generally amenable to derivatization at its two terminals. This limits the number of other functional molecules (e.g. those helpful for protein or drug delivery to specific tissues) that can be conjugated to PEG.

Polyglutamic acid (PGA) is another polymer of choice for solubilizing hydrophobic anticancer drugs. Some anticancer drugs conjugated to PGA have been reported. See Chun Li. *Adv. Drug Del. Rev*, (2002) 54:695-713. However, none of these PGA polymers are currently FDA-approved.

Paclitaxel, extracted from the bark of the Pacific Yew tree (Wani et al., *J Am Chem. Soc.* (1971) 93:2325-7), is a FDA-approved drug for the treatment of ovarian cancer and breast cancer. However, like other anticancer drugs, paclitaxel suffers from poor bio-availability due to its hydrophobicity and insolubility in aqueous solution. One way to solubilize paclitaxel is to formulate it in a mixture of Cremophor-EL and dehydrated ethanol (1:1, v/v) (Sparreboom et al., *Cancer Research* (1999) 59:1454-1457). This formulation is currently commercialized as Taxol® (Bristol-Myers Squibb). Another method of solubilizing paclitaxel is by emulsification using high-shear homogenization (Constantinides et al., *Pharmaceutical Research* (2000) 17:175-182). Polymer-paclitaxel conjugates have been advanced in several clinical trials (Ruth Duncan, *Nature Reviews Drug Discovery* (2003) 2:347-360). Paclitaxel has been formulated into nano-particles with human albumin protein, which has been used in clinical studies (Damascelli et al., *Cancer.* (2001) 92:2592-602, and Ibrahim et al., *Clin Cancer Res*. (2002) 8:1038-44). This formulation is currently commercialized as Abraxane® (American Pharmaceutical Partners, Inc.).

SUMMARY

Relatively hydrophobic drugs (such as certain hydrophobic anticancer drugs, therapeutic proteins and polypeptides) often suffer from poor bioavailability. It is believed that this problem is due at least in part to the poor solubility of these drugs in aqueous systems. Certain enzymatically degradable drugs also suffer from poor bioavailability because they are degraded relatively rapidly in the circulatory system, resulting in rapid elimination from the body. Additionally, controlled release of paclitaxel from a polymer conjugate has yet to be optimized.

The inventors have discovered a series of novel poly-glutamate-amino acids that are capable of conjugating to drugs, including anti-cancer drugs, via a linker as well as a way to provide a controlled release of the drugs through incorporation of a linker between a recurring unit of the polymer and a compound that can include a drug (for example, an anti-cancer drug). In some embodiments, the polymers conjugates preferentially accumulate in certain tissues (e.g., tumor tissues) and/or certain receptors, and thus are useful for delivering drugs to specific parts of the body (e.g., anti-cancer drugs to tumors). In some embodiments, the polymer conjugates can form nanoparticles that can effectively solubilize the anti-cancer agent in an aqueous system by dispersing it at a molecular level, and thereby increasing functionality and/or bioavailability.

Some embodiments described herein relate to a polymer conjugate that can include a recurring unit of Formula (I) and a recurring unit Formula (II):

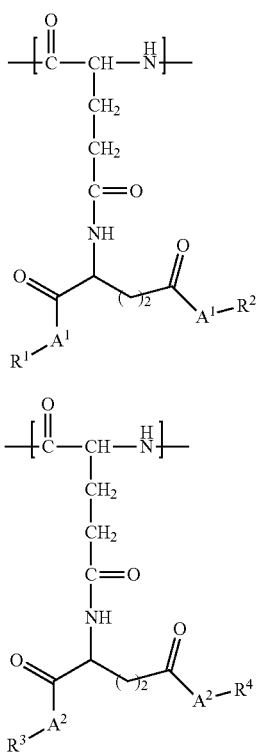

(I)

(II)

wherein: each $A^1$ and each $A^2$ can be independently oxygen or $NR^5$, wherein $R^5$ can be hydrogen or $C_{1-4}$ alkyl; and each $R^1$ and each $R^2$ can be independently selected from hydrogen, a $C_{1-10}$ alkyl group, a $C_{6-20}$ aryl group, ammonium, an alkali metal, and a compound that can include a linker and an anticancer drug; provided that at least one of $R^1$ and $R^2$ is a compound that can include a linker and an anticancer drug; and each $R^3$ and each $R^4$ can be independently selected hydrogen, a $C_{1-10}$ alkyl group, a $C_{6-20}$ aryl group, ammonium, and an alkali metal. In some embodiments, the linker can have the structure:

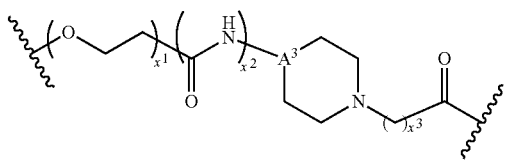

wherein $A^3$ can be independently selected from N or CH; $X^1$ can be 1, 2, 3, 4, 5 or 6; $X^2$ can be 0 or 1; and $X^3$ can be 1, 2 or 3.

Other embodiments described herein relate to a pharmaceutical composition that can include one or more polymer conjugates described herein, and further can include at least one selected from a pharmaceutically acceptable excipient, a carrier, and a diluent.

Still other embodiments described herein relate to a method of treating or ameliorating a disease or condition that can include administering an effective amount of one or more polymer conjugates described herein to a mammal in need thereof. In some embodiments, the disease or condition can be cancer or a tumor.

These and other embodiments are described in greater detail below

DETAILED DESCRIPTION

Figure 1:
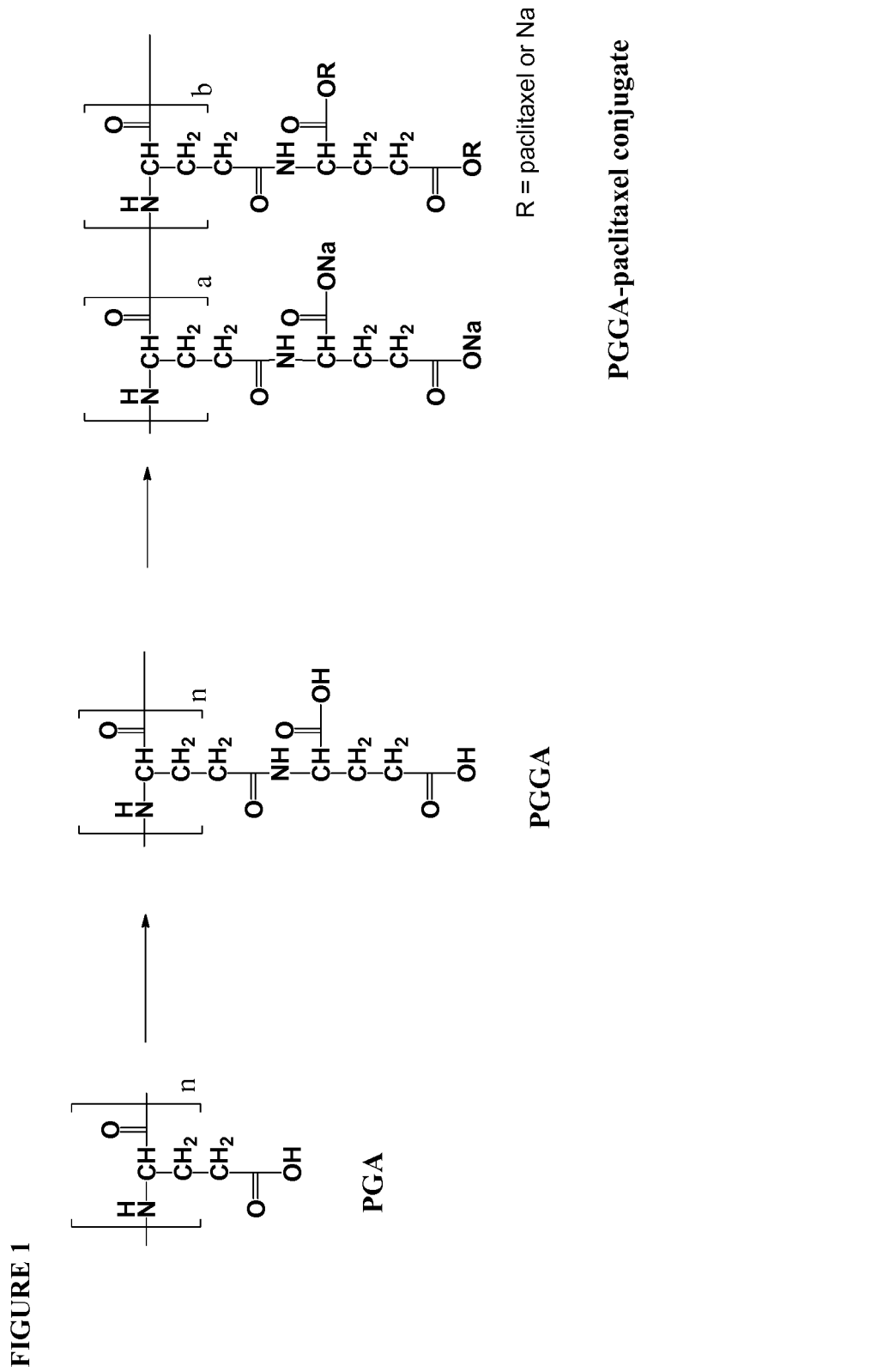
FIG. 1 illustrates a reaction scheme for the preparation of a poly(L-γ-glutamyl-glutamine)-paclitaxel (PTX) conjugate.
Figure 2:
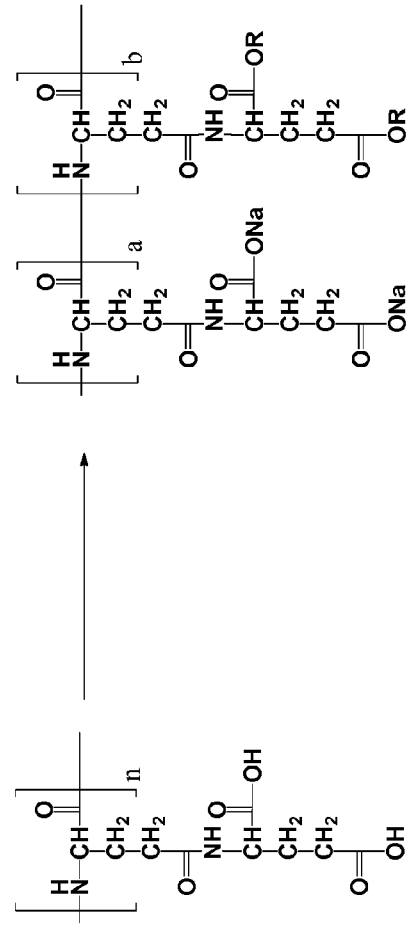
FIG. 2 illustrates a reaction scheme for the preparation of a poly(L-γ-glutamyl-glutamine)-Linker A-paclitaxel (PTX) conjugate.
Figure 2:
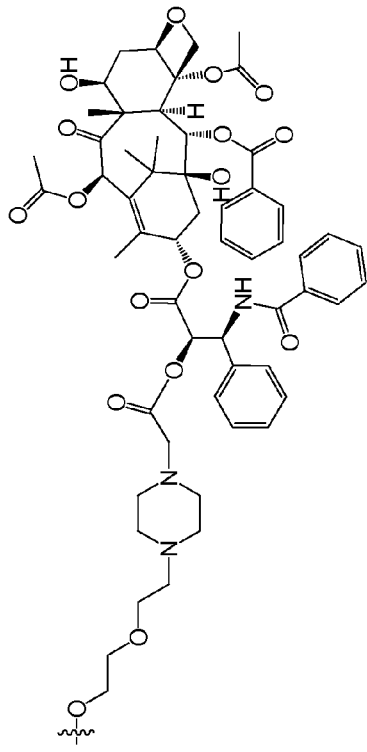

Unless defined otherwise, all technical and scientific terms used herein have the same meaning as is commonly understood by one of ordinary skill in the art. All patents, applications, published applications and other publications referenced herein are incorporated by reference in their entirety unless stated otherwise. In the event that there are a plurality of definitions for a term herein, those in this section prevail unless stated otherwise.

The term "ester" is used herein in its ordinary sense, and thus includes a chemical moiety with formula —$(R)_n$—COOR', where R and R' are independently selected from the group consisting of alkyl, cycloalkyl, aryl, heteroaryl (bonded through a ring carbon) and heteroalicyclic (bonded through a ring carbon), and where n is 0 or 1.

The term "amide" is used herein in its ordinary sense, and thus includes a chemical moiety with formula —$(R)_n$—C(O)NHR' or —$(R)_n$—NHC(O)R', where R and R' are independently selected from the group consisting of alkyl, cycloalkyl, aryl, heteroaryl (bonded through a ring carbon) and heteroalicyclic (bonded through a ring carbon), and where n is 0 or 1. An amide may be included in an amino acid or a peptide molecule attached to drug molecule as described herein, thereby forming a prodrug.

Any amine, hydroxy, or carboxyl side chain on the compounds disclosed herein can be esterified or amidified. The procedures and specific groups to be used to achieve this end are known to those of skill in the art and can readily be found in reference sources such as Greene and Wuts, Protective Groups in Organic Synthesis, 3$^{rd}$ Ed John Wiley & Sons, New York, N.Y., 1999, which is incorporated herein in its entirety.

As used herein, "alkyl" refers to a straight or branched hydrocarbon chain that comprises a fully saturated (no double or triple bonds) hydrocarbon group. The alkyl group may have 1 to 20 carbon atoms (whenever it appears herein, a numerical range such as "1 to 20" refers to each integer in the given range; e.g., "1 to 20 carbon atoms" means that the alkyl group may consist of 1 carbon atom, 2 carbon atoms, 3 carbon atoms, etc., up to and including 20 carbon atoms, although the present definition also covers the occurrence of the term "alkyl" where no numerical range is designated). The alkyl group may also be a medium size alkyl having 1 to 10 carbon atoms. The alkyl group could also be a lower alkyl having 1 to 5 carbon atoms. The alkyl group of the compounds may be designated as "$C_1$-$C_4$ alkyl" or similar designations. By way of example only, "$C_1$-$C_4$ alkyl" indicates that there are one to four carbon atoms in the alkyl chain, i.e., the alkyl chain is selected from the group consisting of methyl, ethyl, propyl, iso-propyl, n-butyl, iso-butyl, sec-butyl, and t-butyl. Typical alkyl groups include, but are in no way limited to, methyl, ethyl, propyl, isopropyl, butyl, isobutyl, tertiary butyl, pentyl, hexyl, and the like.

The alkyl group may be substituted or unsubstituted. When substituted, the substituent group(s) is(are) one or more group(s) individually and independently selected from alkenyl, alkynyl, cycloalkyl, cycloalkenyl, cycloalkynyl, aryl, heteroaryl, heteroalicyclyl, aralkyl, heteroaralkyl, (heteroalicyclyl)alkyl, hydroxy, protected hydroxyl, alkoxy, aryloxy, acyl, ester, mercapto, alkylthio, arylthio, cyano, halogen, carbonyl, thiocarbonyl, O-carbamyl, N-carbamyl, O-thiocarbamyl, N-thiocarbamyl, C-amido, N-amido, S-sulfonamido, N-sulfonamido, C-carboxy, protected C-carboxy, O-carboxy, isocyanato, thiocyanato, isothiocyanato, nitro, silyl, sulfenyl, sulfinyl, sulfonyl, haloalkyl (e.g., mono-, di- and tri-haloalkyl), haloalkoxy (e.g., mono-, di- and tri-haloalkoxy), trihalomethanesulfonyl, trihalomethanesulfonamido, and amino, including mono- and di-substituted amino groups, and the protected derivatives thereof. Wherever a substituent is described as being "optionally substituted" that substitutent may be substituted with one of the above substituents.

As used herein, "aryl" refers to a carbocyclic (all carbon) monocyclic or multicyclic aromatic ring system that has a fully delocalized pi-electron system. Examples of aryl groups include, but are not limited to, benzene, naphthalene and azulene. An aryl group of this invention may be substituted or unsubstituted. When substituted, hydrogen atoms are replaced by substituent group(s) that is(are) one or more group(s) independently selected from alkyl, alkenyl, alkynyl, cycloalkyl, cycloalkenyl, cycloalkynyl, aryl, heteroaryl, heteroalicyclyl, aralkyl, heteroaralkyl, (heteroalicyclyl)alkyl, hydroxy, protected hydroxy, alkoxy, aryloxy, acyl, ester, mercapto, cyano, halogen, thiocarbonyl, O-carbamyl, N-carbamyl, O-thiocarbamyl, N-thiocarbamyl, C-amido, N-amido, S-sulfonamido, N-sulfonamido, C-carboxy, protected C-carboxy, O-carboxy, isocyanato, thiocyanato, isothiocyanato, nitro, silyl, sulfenyl, sulfinyl, sulfonyl, haloalkyl, haloalkoxy, trihalomethanesulfonyl, trihalomethanesulfonamido, and amino, including mono- and di-substituted amino groups, and the protected derivatives thereof, unless the substituent groups are otherwise indicated.

The polymer conjugate can contain one or more chiral carbon atoms. The chiral carbon (which may be indicated by an asterisk *) can have the rectus (right handed) or the sinister (left handed) configuration, and thus the recurring unit may be racemic, enantiomeric or enantiomerically enriched. The symbols "n" and "*" (designating a chiral carbon), as used elsewhere herein, have the same meaning as specified above, unless otherwise stated.

It is understood that, in any compound described herein having one or more chiral centers, if an absolute stereochemistry is not expressly indicated, then each center may independently be of R-configuration or S-configuration or a mixture thereof. Thus, the compounds provided herein may be enantiomerically pure or be stereoisomeric mixtures. In addition it is understood that, in any compound described herein having one or more double bond(s) generating geometrical isomers that can be defined as E or Z each double bond may independently be E or Z a mixture thereof. Likewise, all tautomeric forms are also intended to be included.

Some embodiments described herein relate to a polymer conjugate that can include a recurring unit of Formula (I) and a recurring unit Formula (II):

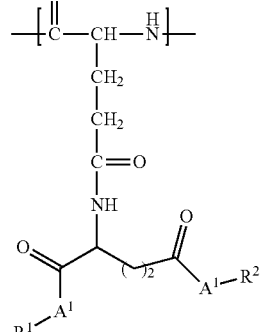

(I)

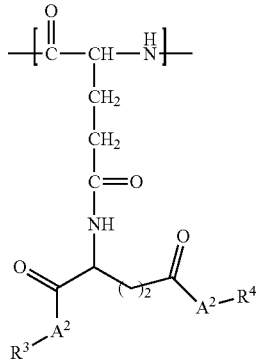

(II)

wherein: each $A^1$ and each $A^2$ can be independently oxygen or $NR^5$, wherein $R^5$ can be hydrogen or $C_{1-4}$ alkyl; and each $R^1$ and each $R^2$ can be independently selected from hydrogen, a $C_{1-10}$ alkyl group, a $C_{6-20}$ aryl group, ammonium, an alkali metal, and a compound that can include a linker and an anticancer drug; provided that at least one of $R^1$ and $R^2$ is a compound that can include a linker and an anticancer drug; and each $R^3$ and each $R^4$ can be independently selected from hydrogen, a $C_{1-10}$ alkyl group, a $C_{6-20}$ aryl group, ammonium, and an alkali metal.

In some embodiments, the linker can have the structure:

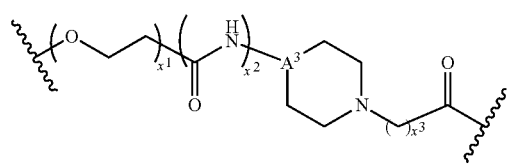

wherein $A^3$ can be independently selected from N or CH; $X^1$ can be 1, 2, 3, 4, 5 or 6; $X^2$ can be 0 or 1; and $X^3$ can be 1, 2 or 3. Table 1 provides some embodiments of the linker. For example, as provided by the first entry in Table 1, in some embodiments, $X^1$ can be 1, $X^2$ can be 0, $X^3$ can be 1 and $A^3$ can be N (nitrogen).

TABLE 1

| Entry | $X^1$ | $X^2$ | $X^3$ | $A^3$ |
|---|---|---|---|---|
| 1 | 1 | 0 | 1 | N |
| 38 | 1 | 0 | 1 | CH |
| 2 | 1 | 1 | 1 | N |
| 3 | 1 | 1 | 1 | CH |
| 4 | 1 | 0 | 2 | N |
| 5 | 1 | 0 | 2 | CH |
| 6 | 1 | 1 | 2 | N |
| 7 | 1 | 1 | 2 | CH |
| 8 | 1 | 0 | 3 | N |
| 9 | 1 | 0 | 3 | CH |
| 10 | 1 | 1 | 3 | N |
| 11 | 1 | 1 | 3 | CH |
| 12 | 2 | 0 | 1 | N |
| 13 | 2 | 0 | 1 | CH |
| 14 | 2 | 1 | 1 | N |
| 15 | 2 | 1 | 1 | CH |
| 16 | 2 | 0 | 2 | N |
| 17 | 2 | 0 | 2 | CH |
| 18 | 2 | 1 | 2 | N |
| 19 | 2 | 1 | 2 | CH |
| 20 | 2 | 0 | 3 | N |
| 21 | 2 | 0 | 3 | CH |
| 22 | 2 | 1 | 3 | N |
| 23 | 2 | 1 | 3 | CH |
| 24 | 3 | 0 | 1 | N |
| 25 | 3 | 0 | 1 | CH |
| 26 | 3 | 1 | 1 | N |
| 27 | 3 | 1 | 1 | CH |
| 28 | 3 | 0 | 2 | N |
| 29 | 3 | 0 | 2 | CH |
| 30 | 3 | 1 | 2 | N |
| 31 | 3 | 1 | 2 | CH |
| 32 | 3 | 0 | 3 | N |
| 33 | 3 | 0 | 3 | CH |
| 34 | 3 | 1 | 3 | N |
| 35 | 3 | 1 | 3 | CH |
| 36 | 4 | 0 | 1 | N |
| 37 | 4 | 0 | 1 | CH |
| 39 | 4 | 1 | 1 | N |
| 40 | 4 | 1 | 1 | CH |
| 41 | 4 | 0 | 2 | N |
| 42 | 4 | 0 | 2 | CH |
| 43 | 4 | 1 | 2 | N |
| 44 | 4 | 1 | 2 | CH |
| 45 | 4 | 0 | 3 | N |
| 46 | 4 | 0 | 3 | CH |
| 47 | 4 | 1 | 3 | N |
| 48 | 4 | 1 | 3 | CH |
| 49 | 5 | 0 | 1 | N |
| 50 | 5 | 0 | 1 | CH |
| 51 | 5 | 1 | 1 | N |
| 52 | 5 | 1 | 1 | CH |
| 53 | 5 | 0 | 2 | N |
| 54 | 5 | 0 | 2 | CH |
| 55 | 5 | 1 | 2 | N |
| 56 | 5 | 1 | 2 | CH |
| 57 | 5 | 0 | 3 | N |
| 58 | 5 | 0 | 3 | CH |
| 59 | 5 | 1 | 3 | N |
| 60 | 5 | 1 | 3 | CH |
| 61 | 6 | 0 | 1 | N |
| 62 | 6 | 0 | 1 | CH |
| 63 | 6 | 1 | 1 | N |
| 64 | 6 | 1 | 1 | CH |
| 65 | 6 | 0 | 2 | N |
| 66 | 6 | 0 | 2 | CH |
| 67 | 6 | 1 | 2 | N |
| 68 | 6 | 1 | 2 | CH |
| 69 | 6 | 0 | 3 | N |
| 70 | 6 | 0 | 3 | CH |
| 71 | 6 | 1 | 3 | N |
| 72 | 6 | 1 | 3 | CH |

In some embodiments, $X^1$ can be 2, $X^2$ can be 0, $A^3$ can be N, and $X^3$ can be 1. In other embodiments, $X^1$ can be 2, $X^2$ can be 0, $A^3$ can be N, and $X^3$ can be 2. In still other embodiments, $X^1$ can be 4, $X^2$ can be 1, $A^3$ can be CH, and $X^3$ can be 1. In some embodiments, the linker can be selected from

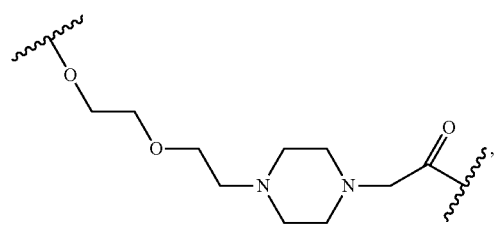

("Linker A")

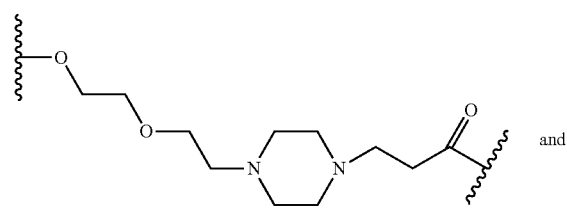

("Linker B")

and

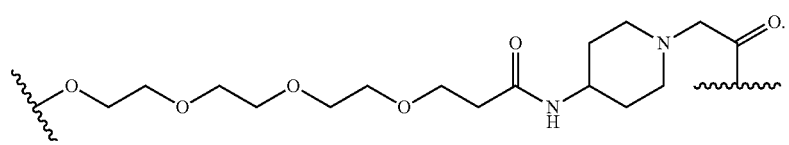

("Linker C")

For Linkers A, B and C, the left side of the linker group can be attached to a recurring unit of Formula (I) and the right side of the linker group can be attached to an anticancer drug.

In some embodiments, a recurring unit of Formula (I) can have the structure:

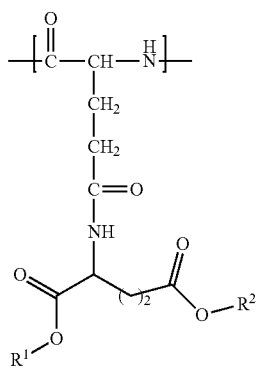

and a recurring unit of Formula (II) can have the structure:

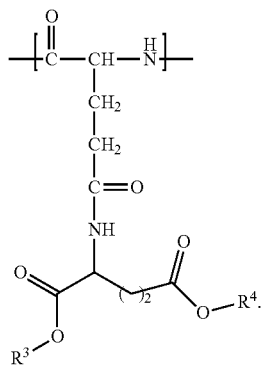

In some embodiments, the other one of $R^1$ and $R^2$ can be an alkali metal, each $R^3$ and each $R^4$ can be an alkali metal. Examples of suitable alkali metal include lithium (Li), sodium (Na), potassium (K), rubidium (Rb), and cesium (Cs). In some embodiments, the alkali metal can be sodium. In other embodiments, the other one of $R^1$ and $R^2$ can be hydrogen, and each $R^3$ and each $R^4$ can be hydrogen.

Various anticancer drugs can be conjugated to a recurring unit of Formula (I) via a linker described herein. In some embodiments, the anticancer drug can be selected from a taxane, a camptotheca, and an anthracycline. When the agent comprises a taxane, the taxane can be paclitaxel. In other embodiments, the taxane can be docetaxel. When the anticancer drug is paclitaxel, paclitaxel may be conjugated to the recurring unit of Formula (I) at the oxygen atom via the C2'-carbon of the paclitaxel. Alternatively or in addition, paclitaxel may be conjugated to the recurring unit of Formula (I) at the oxygen atom via the C7-carbon of the paclitaxel. When the anticancer drug is a camptotheca, the camptotheca can be camptothecin. In some embodiments, when the anticancer drug is an anthracycline, the anthracycline can be doxorubicin.

The amount of an anticancer drug present in the polymer conjugate can vary over a wide range. In some embodiments, the polymer conjugate can include an amount of the anticancer drug (excluding the linker) in the range of about 1% to about 50% (weight/weight) based on the mass ratio of the anticancer drug to the polymer conjugate. In other embodiments, the polymer conjugate can include an amount of the anticancer drug (excluding the linker) in the range of about 5% to about 40% (weight/weight) based on the mass ratio of the anticancer drug to the polymer conjugate. In still other embodiments, the polymer conjugate can include an amount of the anticancer drug (excluding the linker) in the range of about 10% to about 30% (weight/weight). In yet still other embodiments, the polymer conjugate can include an amount of the anticancer drug (excluding the linker) in the range of about 1% to about 10% (weight/weight), about 1% to about 5% (weight/weight), about 5% to about 10% (weight/weight), about 10% to about 20% (weight/weight), about 15% to about 35% (weight/weight), about 30% to about 40% (weight/weight) and the like, based on the mass ratio of the anticancer drug to the polymer conjugate. In some embodiments, the polymer conjugate can include an amount of the anticancer drug (excluding the linker) in about 20% (weight/weight) based on the mass ratio of the anticancer drug to the polymer conjugate. In other embodiments, the polymer conjugate can include an amount of the anticancer drug (excluding the linker) of 5% (weight/weight), about 10% (weight/weight) 15% (weight/weight), about 25% (weight/weight), about 30% (weight/weight) and the like based on the mass ratio of the anticancer drug to the polymer conjugate.

The total number of recurring units of Formula (I) and Formula (II) can vary. In some embodiments, the total number of recurring units of Formula (I) and Formula (II) can be in the range of from about 50 to about 5,000. In other embodiments, the total number of recurring units of Formula (I) and Formula (II) can be in the range of from about 100 to about 2,000. In still other embodiments, the total number of recurring units of Formula (I) and Formula (II) can be in the range of from about 150 to about 15,000, from about 50 to about 2,000, from about 300 to about 6,000, and the like.

Likewise, the percentage of recurring units of each of Formulae (I) and (II) individually in the polymer conjugate may vary over a wide range. Table 2 provides some embodiments of a polymer conjugate that can include recurring units of Formula (I) and recurring units of Formula (II). For example, as provided by the first entry in Table 2, in some embodiments, a polymer conjugate can include about 1 mole % to about 60 mole % of the recurring unit of Formula (I) based on the total moles of recurring units of Formulae (I) and (II). As another embodiment, as provided by entry 9, in some embodiments, a polymer conjugate can include at least about 10 mole % of the recurring unit of Formula (I) based on the total moles of recurring units of Formulae (I) and (II). The basis for the embodiments in Table 2 is the total moles of recurring units of Formulae (I) and (II) in the polymer conjugate.

TABLE 2

| Entry | Mole % of Formula (I) | Entry | Mole % of Formula (II) |
|---|---|---|---|
| 1 | about 1% to about 60% | 13 | about 1% to about 70% |
| 2 | about 1% to about 10% | 14 | about 1% to about 10% |
| 3 | about 1% to about 20% | 15 | about 1% to about 20% |
| 4 | about 1% to about 30% | 16 | about 1% to about 30% |
| 5 | about 5% to about 50% | 17 | about 1% to about 50% |
| 6 | about 10% to about 30% | 18 | about 20% to about 70% |
| 7 | about 30% to about 40% | 19 | about 40% to about 60% |
| 8 | about 20% to about 70% | 20 | about 50% to about 60% |
| 9 | at least about 10% | 21 | at least about 20% |
| 10 | at least about 25% | 22 | at least about 40% |
| 11 | no more than about 40% | 23 | no more than about 70% |
| 12 | no more than about 30% | 24 | no more than about 60% |

The polymer conjugates that include a recurring unit of Formula (I) and a recurring unit of Formula (II) are copolymers. In some embodiments, a polymer conjugate described herein can include two or more different recurring units of Formula (I) and/or two or more different recurring units of Formula (II). Further, in some embodiments, polymer conjugates that can include a recurring unit of Formula (I) and a recurring unit of Formula (II) may include other recurring units that are not of Formula (I) and/or not of Formula (II). For example, a recurring unit of Formula (III) may also be present

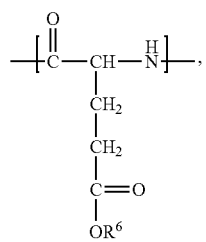

wherein $R^6$ can be selected from hydrogen, ammonium and an alkali metal (including those alkali metals described herein). In other embodiments, polymers may only consist of recurring units of Formula (I) and Formula (II).

The weight average molecular weight of polymer conjugates that include a recurring unit of Formula (I) and a recurring unit of Formula (II) can vary. In some embodiments, the weight average molecular weight of the polymer conjugate can be in the range of about 20 kDa to about 150 kDa. In other embodiments, the weight average molecular weight of the polymer conjugate can be in the range of about 60 kDa to about 90 kDa. In still other embodiments, the weight average molecular weight of the polymer conjugate can be in the range of about 35 kDa to about 85 kDa. In yet still other embodiments, the weight average molecular weight of the polymer conjugate can be in the range of about 50 kDa to about 65 kDa. In some embodiments, the weight average molecular weight of the polymer conjugate can be in the range of about 45 kDa to about 70 kDa, about 35 kDa to about 100 kDa, about 40 kDa to about 150 kDa, about 50 kDa to about 85 kDa, about 70 kDa to about 85 kDa, about 50 kDa to about 60 kDa, and the like. In some embodiments, the weight average molecular weight of the polymer conjugate can be at least about 40 kDa. In other embodiments, the weight average molecular weight of the polymer conjugate can be at least about 50 kDa. In other embodiments, the weight average molecular weight of the polymer conjugate can be at least about 60 kDa. In still other embodiments, the weight average molecular weight of the polymer conjugate can be less than about 80 kDa. In yet still other embodiments, the weight average molecular weight of the polymer conjugate can be less than about 70 kDa.

The polymers described herein may be formed into nanoparticles in aqueous solution. Conjugates that include a polymer described herein that include an anticancer drug and a linker may be formed into nanoparticles in a similar manner. Such nanoparticles may be used to preferentially deliver a drug to a selected tissue.

In some embodiments, the amount of the anticancer drug and the percentage amounts of the recurring units of Formula (I) and Formula (II), as well as the linker may be selected to advantageously control the solubility of the resulting polymer conjugate. For example, in some embodiments, the amount of the drug and the percentage amounts of the recurring units of Formula (I) and Formula (II) are selected so that the polymer conjugate is soluble (or insoluble) at a particular pH and/or pH range of interest. In some embodiments, the molecular weight of the polymer is also selected to control solubility. Examples provided below illustrate control over solubility (as well as degradation behavior) by appropriate selection of the amount of the anticancer drug, the percentage amounts of the recurring units of Formula (I) and Formula (II) and the linker. Those skilled in the art, informed by the guidance provided herein, can use routine experimentation to identify suitable amounts of the anticancer drug, the percentage amounts of the recurring units of Formula (I) and Formula (II) and a linker that results in a polymer conjugate with desired solubility characteristics. Such control over solubility may be advantageous, depending on the application. For example, embodiments of the polymer conjugates provided herein may be used to provide improved delivery of otherwise poorly soluble anticancer drugs to selected tissues, preferably reducing undesired side effects, and/or may reduce the frequency at which a subject needs to take the anticancer drug.

The amount of the anticancer drug, the linker and the percentage amounts of the recurring units of Formula (I) and Formula (II) can be preferably selected to provide a polymer conjugate solubility that is greater than that of a comparable polyglutamic acid conjugate that comprises substantially the same amount of the same anticancer drug. In some embodiments, the polymer conjugate solubility is greater than that of a comparable polyglutamic acid conjugate. Solubility is measured by forming a polymer conjugate solution comprising at least 5 mg/mL of the polymer conjugate in 0.9 wt. % aqueous NaCl at about 22° C., and determining the optical clarity. Optical clarity may be determined turbidimetrically, e.g., by visual observation or by appropriate instrumental methods known to those skilled in the art. Comparison of the resulting solubility to a similarly formed polyglutamic acid conjugate solution shows improved solubility as evidenced by greater optical clarity over a broader range of pH values. Thus, a polymer conjugate solubility is greater than that of a comparable polyglutamic acid conjugate that comprises substantially the same amount of the anticancer drug when a tested polymer conjugate solution, comprising at least 5 mg/mL of the polymer conjugate in 0.9 wt. % aqueous NaCl at about 22° C., has greater optical clarity over a broader pH range than that of a comparable tested polyglutamic acid conjugate solution. Those skilled in the art will understand that a "comparable" polyglutamic acid conjugate is a control material in which the polymeric portion of the conjugate has a molecular weight that is approximately the same as that of the subject polymer conjugate (comprising a recurring unit of Formula (I) and a recurring unit of Formula (II)) to which it is being compared.

In some embodiments, the amount of the anticancer drug, the linker, the percentage of the recurring unit of Formula (I) and the percentage of the recurring unit of Formula (II) in the polymer conjugate can be selected to provide a polymer conjugate solubility that is greater than that of a comparable polyglutamic acid conjugate that comprises substantially the same amount of the anticancer drug. The range of pH values over which the polymer conjugate, comprising recurring units of Formula (I) and Formula (II) has greater solubility than that of a comparable polyglutamic acid conjugate may be narrow or broad. As noted above, solubility is measured by forming a polymer conjugate solution comprising at least 5 mg/mL of the polymer conjugate in 0.9 wt. % aqueous NaCl at about 22° C., and determining the optical clarity. In some embodiments, the polymer conjugate can be soluble over a pH range of at least about 3 pH units. In other embodiments, the polymer conjugate can be soluble over a pH range of at least about 8 pH units. In still other embodiments, the polymer conjugate can be soluble over a pH range of at least about 9 pH units. In yet still other embodiments, the pH range over which the polymer conjugate can be soluble includes at least one pH value in the range of about 2 to about 5, e.g., at pH=2, pH=3, pH=4 and/or pH=5. Preferably, the pH range over which the polymer conjugate is soluble is broader than the pH range over which the comparable polyglutamic acid conjugate is soluble. For example, in some embodiments, the polymer conjugate can be soluble over a pH range that is at least about one pH unit broader, preferably at least about two pH units broader, than the pH range over which the comparable polyglutamic acid conjugate is soluble.

The amount of polymer conjugate placed in solution to measure solubility can also vary greatly. In some embodiments, solubility can be measured when the tested polymer conjugate solution comprises at least about 5 mg/mL of the polymer conjugate. In other embodiments, solubility can be measured when the tested polymer conjugate solution comprises at least about 10 mg/mL of the polymer conjugate. In still other embodiments, solubility can be measured when the tested polymer conjugate solution comprises at least about 25 mg/mL of the polymer conjugate. In yet still other embodiments, solubility can be measured when the tested polymer conjugate solution comprises at least about 100 mg/mL of the polymer conjugate. In some embodiments, solubility can be measured when the tested polymer conjugate solution comprises at least about 150 mg/mL of the polymer conjugate. Those skilled in the art will understand that the comparable polyglutamic acid conjugate is tested at about the same concentration as that of the tested polymer conjugate.

Surprisingly, in some embodiments, a polymer conjugate that includes a recurring unit of Formula (I) and a recurring unit of Formula (II) can release a greater amount of the anticancer drug in approximately the same amount of time at approximately the same temperature as compared to a comparable poly(L-γ-glutamyl-glutamine)-(anticancer drug) conjugate. As used herein, a "comparable poly(L-γ-glutamyl-glutamine)-(anticancer drug) conjugate" is a control material in which the polymeric portion of the conjugate has a molecular weight that is approximately the same as that of the subject polymer conjugate (comprising a recurring unit of Formula (I) and a recurring unit of Formula (II)) to which it is being compared and includes approximately the same amount of the anticancer drug. In some embodiments, a polymer conjugate containing that includes a recurring unit of Formula (I) and a recurring unit of Formula (II) can release at least about 5% more of the anticancer drug compared to a comparable poly(L-γ-glutamyl-glutamine)-(anticancer drug) conjugate. Table 3 provides further embodiments of a polymer conjugate that can include a recurring unit of Formula (I) and a recurring unit of Formula (II) as compared to a comparable poly(L-γ-glutamyl-glutamine)-(anticancer drug) conjugate. For example, as provided by the first entry in Table 3, in some embodiments, a polymer conjugate that can include a recurring unit\ of Formula (I) and a recurring unit of Formula (II) can release at least about 10% more of the anticancer drug compared to a comparable poly(L-γ-glutamyl-glutamine)-(anticancer drug) conjugate. As a further example, as provided by the fifth entry, in some embodiments, a polymer conjugate that can include a recurring unit of Formula (I) and a recurring unit of Formula (II) can release in the range of about 5% to about 30% more of the anticancer drug compared to a comparable poly(L-γ-glutamyl-glutamine)-(anticancer drug) conjugate.

TABLE 3

| Entry | Increased release of the anticancer drug |
|---|---|
| 1 | ≥ about 10% |
| 2 | ≥ about 15% |
| 3 | ≥ about 20% |
| 4 | ≥ about 25% |
| 5 | about 5% to about 30% |
| 6 | about 10% to about 25% |
| 7 | about 15% to about 20% |

Polymers that can include a recurring unit of Formula (I) and a recurring unit of Formula (II) may be prepared in various ways. In some embodiments, a recurring unit of Formula (I) and a recurring unit of Formula (II) can be produced starting with polyglutamic acid and an amino acid, such glutamic acid. Alternatively, in other embodiments, the polymer may be created by first converting the starting polyglutamic acid material into its salt form. The salt form of polyglutamic can be obtained by reacting polyglutamic acid with a suitable base, e.g., sodium bicarbonate. An amino acid moiety or its salt form (for example, glutamic acid or glutamate) can be attached to the pendant carboxylic acid group of the polyglumatic acid. The weight average molecular weight of the polyglutamic acid may vary over a broad range, but is preferably from about 10,000 to about 200,000 daltons, and more preferably from about 25,000 to about 100,000 daltons.

In some embodiments, the amino acid, such as glutamic, can be protected by a protecting group before attachment to the polyglutamic acid or polyglutamate. One example of a protected amino acid moiety suitable for this reaction is L-glutamic acid di-t-butyl ester hydrochloride, shown below:

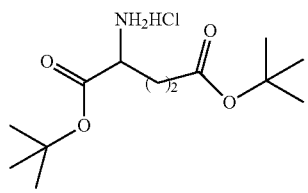

Reaction of the polyglutamic acid or polyglutamate with the amino acid may take place in the presence of any suitable solvent. In some embodiments, the solvent can be an aprotic solvent, for example, N,N'-dimethylformamide (DMF). In some embodiments, a coupling agent such as 1-ethyl-3-(3-dimethylaminopropyl)carbodiimide (EDC), N,N'-Dicyclohexylcarbodiimide (DCC), 1,1'-Carbonyldiimidazole (CDI), N,N-Disuccinimidyl carbonate (D SC), O-(7-Azabenzotriazol-1-yl)-N,N,N',N'-tetramethyluronium hexafluorophosphate (HATU), O-(Benzotriazol-1-yl)-N,N,N',N'-tetramethyluronium hexafluorophosphate (HBTU), O-(6-Chlorobenzotriazol-1-yl)-N,N,N',N'-tetramethyluronium hexafluorophosphate (HCTU), benzotriazol-1-yl-oxytripyrrolidinophosphonium hexafluorophosphate (PyBOP®), Bromo-tris-pyrrolidino phosphoniumhexafluorophosphate (PyBroP®), O-(Benzotriazol-1-yl)-N,N,N',N'-tetramethyluronium tetrafluoroborate (TBTU), and (Benzotriazol-1-yloxy)tris(dimethylamino)phosphonium hexafluorophosphate (BOP) can be used. In other embodiments, the reaction can take place in the presence of a catalyst (e.g., DMAP).

The compound that includes a linker and an anticancer drug can be prepared by a variety of methods. Examples of compounds that include a linker and an anticancer drug that can be used to prepare a recurring unit of Formula (I) include the following:

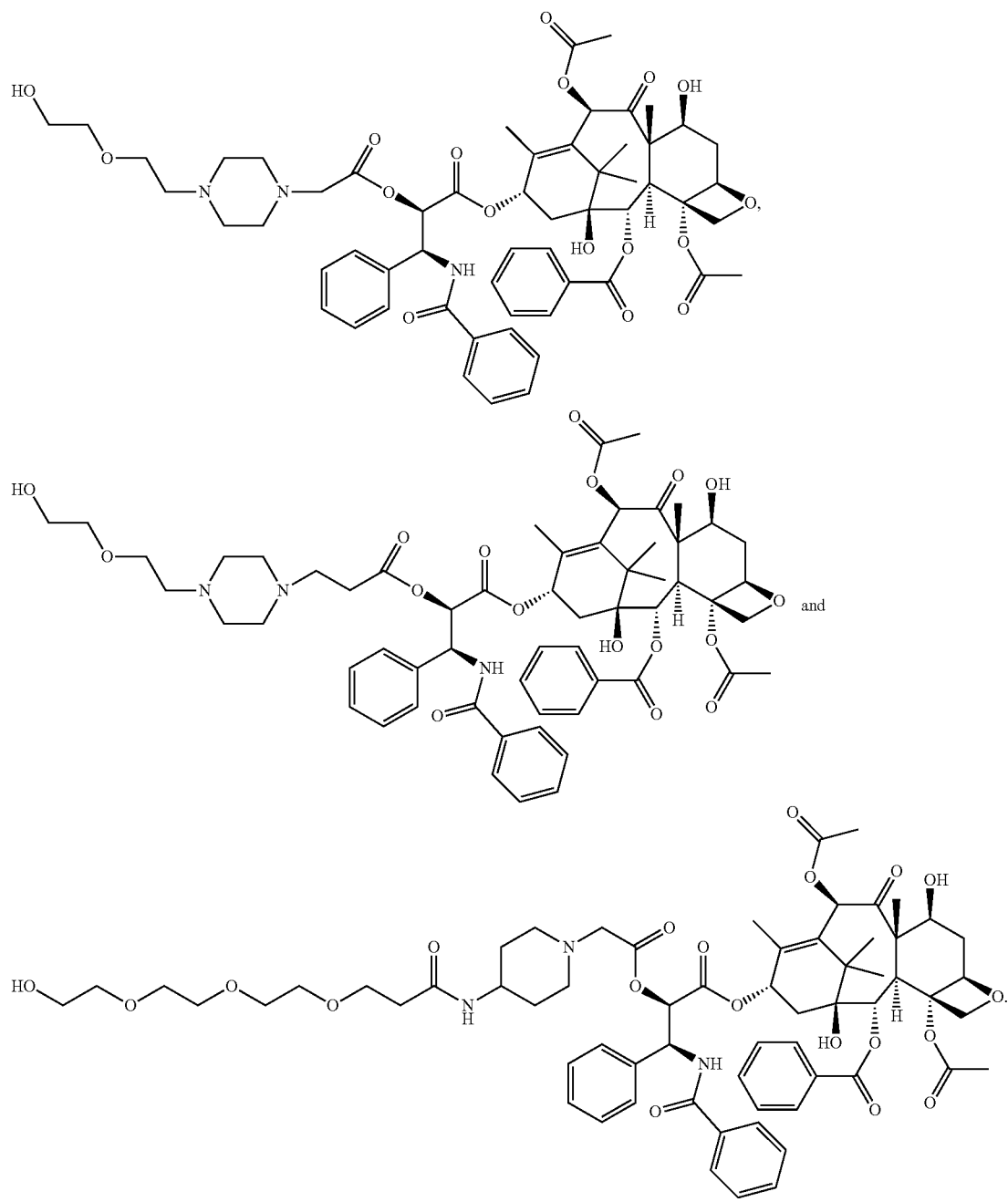

One method for preparing the compound that includes a linker and an anticancer drug is by first attaching the linker to the anticancer drug using one or more methods known to those skilled in the art. One suitable method of forming such a compound is via a coupling reaction, for example, as described in a portion of Example 1 as well as shown in a portion of FIG. 3. If desired and/or needed, the part of the linker that will become attached to the polymer can be protected using one or more suitable protecting groups during at least a portion of the steps when the linker is being attached to the drug. Suitable protecting groups are known in the art, for example, silyl group(s). Alternatively, the linker can be first attached to a recurring unit of the polymer (for example, a recurring unit having the structure of a recurring unit of Formula (II)), and then attaching the anticancer drug to the other end of the linker. As a further alternative, the linker can be reacted with an amino acid, such as glutamic or glutamate, to form a compound in which the linker is appended to the amino acid. Then, the anticancer drug can be attached to the other end of the linker. As described herein, this compound that has the amino acid, such glutamic or glutamate, the linker and the anticancer drug can be then be reacted with polyglutamic acid or its salt to form a recurring unit of Formula (I).

Conjugation of a compound that includes a linker and an anticancer drug to a polymer, such as polyglutamic acid and/or polyglutamate) as described herein may be carried out in various ways. One method for conjugating the compound that includes a linker and an anticancer drug to form a recurring unit of Formula (I) is by using heat (e.g., heat from using a microwave method). Alternatively, conjugation may take place at room temperature. Appropriate solvents, coupling agents, catalysts, and/or buffers as generally known to those skilled in the art and/or as described herein may be used to form the polymer conjugate. As with polyglutamic acid, both the salt or acid form of the polymer obtained from polyglutamic acid and/or salt and an amino acid can be used as starting material for forming the polymer conjugate. In some embodiments, the anticancer drug can be a taxane, a camptotheca, and/or an anthracycline. In some embodiments, the anticancer drug can be a taxane such as paclitaxel or docetaxel. In other embodiments, the anticancer drug conjugated to the polymer can be a camptotheca, such as camptothecin. In still other embodiments, the anticancer drug conjugated to the polymer can be an anthracycline, such as doxorubicin. In some embodiments, the anticancer drug conjugated to the polymer can be paclitaxel, including paclitaxel conjugated to the polymer via its C2'-oxygen atom and/or via its C7-oxygen atom. In some embodiments, the paclitaxel can be coupled to the polymer only by the C2'-oxygen atom. In other embodiments, the paclitaxel can be coupled to the polymer only by the C7-oxygen atom. In still other embodiments, the polymer can include both C2'-conjugated paclitaxel groups and C7-conjugated paclitaxel groups.

In some embodiments, the compound that includes a linker and an anticancer drug can be coupled to a recurring unit of Formula (I) using a coupling agent (e.g., EDC and/or DCC) and/or a catalyst (e.g, DMAP) in a solvent (e.g, an aprotic solvent such as DMF). Additional agents, such as pyridine or hydroxybenzotriazole may be used. In some embodiments, the reaction may take place over the period of 0.5-2 days. Suitable methods known to those skilled in the art can be used to isolate and/or purify the polymer conjugate. For example, the reaction mixture can be poured into an acidic solution to form a precipitate. Any precipitate that forms can then be filtered and washed with water. Optionally, the precipitate can be purified by any suitable method. For example, the precipitate can be transferred into acetone and dissolved, and the resulting solution can be filtered again into a sodium bicarbonate solution. If desired, the resulting reaction solution can be dialyzed in water using a cellulose membrane and the polymer can be lyophilized and isolated. The content of the compound that includes an anticancer drug (such as paclitaxel) in the resulting polymer may be determined by UV spectrometry.

Alternatively, the compound that includes a linker and the anticancer drug can be reacted with an amino acid, such as glutamic acid or glutamate, to form a second compound in which the compound that includes the linker and the anticancer drug is covalently bonded to the amino acid. The amino acid-agent compound can then be reacted with polyglutamic acid or its salt to form a recurring unit of Formula (I). In some embodiments, paclitaxel can be reacted with glutamic acid to form a compound in which the paclitaxel is covalently bonded to the pendant carboxylic acid group of the glutamic acid. The glutamic acid-paclitaxel compound can then be reacted with polyglutamic acid or its salt to form a recurring unit of Formula (I). If desired, the paclitaxel coupled to the amino acid by the C2'-oxygen can be separated from the paclitaxel coupled to the amino acid by the C7-oxygen using known separation methods (e.g, HPLC).

After formation of the polymer conjugate, any free amount of anticancer drug not covalently bonded to the polymer may also be measured. For example, thin layer chromatography (TLC) may be used to confirm the substantial absence of free paclitaxel remaining in the compositions of polymers conjugated to paclitaxel.

If the oxygen atoms of the amino acid are protected, the protecting groups can be removed using known methods such as using a suitable acid (e.g., trifluoroacetic acid). If desired, the salt form of the polymer obtained from reacting polyglutamic acid with the amino acid can be formed by treating the acid form of the polymer with a suitable base solution, e.g., sodium bicarbonate solution. The polymer may be recovered and/or purified by methods known to those skilled in the art. For example, the solvent may be removed by suitable methods, for instance, rotary evaporation. Additionally, the reaction mixture may be filtered into an acidic water solution to induce precipitation. The resultant precipitate can then be filtered, and washed with water. Further information regarding preparation of recurring units of Formulae (I) and (II) are set forth in U.S. Patent Publication No. 2007-0128118, filed Dec. 1, 2006, which is hereby incorporated by reference in its entirety, and particularly for the purpose of describing the synthesis of the polymers described therein.

Pharmaceutical Compositions

Some embodiments described herein relate to a composition that can include one or more polymers conjugates described herein (such as a recurring unit of Formula (I) and a recurring unit of Formula (II)) and at least one selected from a pharmaceutically acceptable excipient, a carrier, and a diluent. In some embodiments, prodrugs, metabolites, stereoisomers, hydrates, solvates, polymorphs, and pharmaceutically acceptable salts of a polymer conjugate disclosed herein are provided.

A "prodrug" refers to an agent that is converted into the parent drug in vivo.

The term "pharmaceutical composition" refers to a mixture of a polymer conjugate described herein with other chemical components, such as diluents or carriers. The pharmaceutical composition facilitates administration of a polymer conjugate to an organism. Multiple techniques of administering a compound exist in the art including, but not limited to, oral, injection, aerosol, parenteral, and topical administration. Pharmaceutical compositions can also be obtained by reacting compounds with inorganic or organic acids such as hydrochloric acid, hydrobromic acid, sulfuric acid, nitric acid, phosphoric acid, methanesulfonic acid, ethanesulfonic acid, p-toluenesulfonic acid, salicylic acid and the like.

The term "carrier" refers to a chemical compound that facilitates the incorporation of a compound into cells or tissues. For example dimethyl sulfoxide (DMSO) is a commonly utilized carrier as it facilitates the uptake of many organic compounds into the cells or tissues of an organism.

The term "diluent" refers to chemical compounds diluted in water that will dissolve the compound of interest (e.g., a polymer conjugate described herein) as well as stabilize the biologically active form of the compound. Salts dissolved in buffered solutions are utilized as diluents in the art. One commonly used buffered solution is phosphate buffered saline because it mimics the salt conditions of human blood. Since buffer salts can control the pH of a solution at low concentrations, a buffered diluent rarely modifies the biological activity of a compound. The term "physiologically acceptable" refers to a carrier or diluent that does not abrogate the biological activity and properties of the compound.

The term "pharmaceutically acceptable salt" refers to a salt of a compound that does not cause significant irritation to an organism to which it is administered and does not abrogate the biological activity and properties of the compound. In some embodiments, the salt is an acid addition salt of the compound. Pharmaceutical salts can be obtained by reacting a compound with inorganic acids such as hydrohalic acid (e.g., hydrochloric acid or hydrobromic acid), sulfuric acid, nitric acid, phosphoric acid and the like. Pharmaceutical salts can also be obtained by reacting a compound with an organic acid such as aliphatic or aromatic carboxylic or sulfonic acids, for example acetic, succinic, lactic, malic, tartaric, citric, ascorbic, nicotinic, methanesulfonic, ethanesulfonic, p-toluenesulfonic, salicylic or naphthalenesulfonic acid. Pharmaceutical salts can also be obtained by reacting a compound with a base to form a salt such as an ammonium salt, an alkali metal salt, such as a sodium or a potassium salt, an alkaline earth metal salt, such as a calcium or a magnesium salt, a salt of organic bases such as dicyclohexylamine, N-methyl-D-glucamine, tris(hydroxymethyl)methylamine, $C_1$-$C_7$ alkylamine, cyclohexylamine, triethanolamine, ethylenediamine, and salts with amino acids such as arginine, lysine, and the like.

If the manufacture of pharmaceutical formulations involves intimate mixing of the pharmaceutical excipients and the active ingredient in its salt form, then it may be desirable to use pharmaceutical excipients which are non-basic, that is, either acidic or neutral excipients.

In some embodiments, the pharmaceutical composition can include one or more physiologically acceptable surface active agents, carriers, diluents, excipients, smoothing agents, suspension agents, film forming substances, and coating assistants, or a combination thereof; and a compound (e.g., a polymer conjugates described herein) disclosed herein. Acceptable carriers or diluents for therapeutic use are well known in the pharmaceutical art, and are described, for example, in Remington's Pharmaceutical Sciences, 18th Ed., Mack Publishing Co., Easton, Pa. (1990), which is incorporated herein by reference in its entirety. Preservatives, stabilizers, dyes, sweeteners, fragrances, flavoring agents, and the like may be provided in the pharmaceutical composition. For example, sodium benzoate, ascorbic acid and esters of p-hydroxybenzoic acid may be added as preservatives. In addition, antioxidants and suspending agents may be used. In various embodiments, alcohols, esters, sulfated aliphatic alcohols, and the like may be used as surface active agents; sucrose, glucose, lactose, starch, crystallized cellulose, mannitol, light anhydrous silicate, magnesium aluminate, magnesium metasilicate aluminate, synthetic aluminum silicate, calcium carbonate, sodium acid carbonate, calcium hydrogen phosphate, calcium carboxymethyl cellulose, and the like may be used as excipients; magnesium stearate, talc, hardened oil and the like may be used as smoothing agents; coconut oil, olive oil, sesame oil, peanut oil, soya may be used as suspension agents or lubricants; cellulose acetate phthalate as a derivative of a carbohydrate such as cellulose or sugar, or methylacetate-methacrylate copolymer as a derivative of polyvinyl may be used as suspension agents; and plasticizers such as ester phthalates and the like may be used as suspension agents.

The pharmaceutical compositions described herein can be administered to a human patient per se, or in pharmaceutical compositions where they are mixed with other active ingredients, as in combination therapy, or carriers, diluents, excipients or combinations thereof. Proper formulation is dependent upon the route of administration chosen. Techniques for formulation and administration of the compounds described herein are known to those skilled in the art.

The pharmaceutical compositions disclosed herein may be manufactured in a manner that is itself known, e.g., by means of conventional mixing, dissolving, granulating, dragee-making, levigating, emulsifying, encapsulating, entrapping or tableting processes. Additionally, the active ingredients are contained in an amount effective to achieve its intended purpose. Many of the compounds used in the pharmaceutical combinations disclosed herein may be provided as salts with pharmaceutically compatible counterions.

Multiple techniques of administering a compound exist in the art including, but not limited to, oral, rectal, topical, aerosol, injection and parenteral delivery, including intramuscular, subcutaneous, intravenous, intramedullary injections, intrathecal, direct intraventricular, intraperitoneal, intranasal and intraocular injections.

In various embodiments, the pharmaceutical compositions and polymer conjugates disclosed herein may be in the form of an injectable liquid.

Injectables can be prepared in conventional forms, either as liquid solutions or suspensions, solid forms suitable for solution or suspension in liquid prior to injection, or as emulsions. Suitable excipients are, for example, water, saline, dextrose, mannitol, lactose, lecithin, albumin, sodium glutamate, cysteine hydrochloride, and the like. In addition, if desired, the injectable pharmaceutical compositions may contain minor amounts of nontoxic auxiliary substances, such as wetting agents, pH buffering agents, and the like. Physiologically compatible buffers include, but are not limited to, Hanks's solution, Ringer's solution, or physiological saline buffer. If desired, absorption enhancing preparations (for example, liposomes), may be utilized.

For transmucosal administration, penetrants appropriate to the barrier to be permeated may be used in the formulation.

Pharmaceutical formulations for parenteral administration, e.g., by bolus injection or continuous infusion, include aqueous solutions of the active compounds (e.g., a polymer disclosed herein) in water-soluble form. Additionally, suspensions of the active compounds may be prepared as appropriate oily injection suspensions. Suitable lipophilic solvents or vehicles include fatty oils such as sesame oil, or other organic oils such as soybean, grapefruit or almond oils, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents that increase the solubility of the compounds to allow for the preparation of highly concentrated solutions. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle, e.g., sterile pyrogen-free water, before use.

One may also administer the compound in a local rather than systemic manner, for example, via injection of the compound directly into the infected area, often in a depot or sustained release formulation. Furthermore, one may administer the compound in a targeted drug delivery system, for example, in a liposome coated with a tissue-specific antibody. The liposomes will be targeted to and taken up selectively by the organ.

The pharmaceutical compositions may, if desired, be presented in a pack or dispenser device which may contain one or more unit dosage forms containing the active ingredient. The pack may for example comprise metal or plastic foil, such as a blister pack. The pack or dispenser device may be accompanied by instructions for administration. The pack or dispenser may also be accompanied with a notice associated with the container in form prescribed by a governmental agency regulating the manufacture, use, or sale of pharmaceuticals, which notice is reflective of approval by the agency of the form of the drug for human or veterinary administration. Such notice, for example, may be the labeling approved by the U.S. Food and Drug Administration for prescription drugs, or the approved product insert. Compositions that can include a compound described herein formulated in a compatible pharmaceutical carrier may also be prepared, placed in an appropriate container, and labeled for treatment of an indicated condition.

Methods of Administration

Some embodiments described herein relate to a method of treating or ameliorating a disease or condition that can include administering an effective amount of one or more of the polymer conjugates described herein (for example, a polymer conjugate that can include a recurring unit of Formula (I) and a recurring unit of Formula (II)) or one or more of the pharmaceutical compositions described herein to a subject in need thereof. Other embodiments described herein relate to using a polymer conjugate described herein to deliver an anticancer drug to a selected tissue. In some embodiments, the polymer conjugates that can include a recurring unit of Formula (I) and a recurring unit of Formula (II) can be used to treat or ameliorate a disease or condition, such as cancer. In other embodiments, a polymer conjugate described herein can be used to form a medicament that can be used to treat or ameliorate a disease or condition, for example, cancer. In still other embodiments, a polymer conjugate described herein can be used to treat or ameliorate a disease or condition, including cancer. In some embodiments, the disease or condition can be a cancer such as lung cancer, breast cancer, colon cancer, ovarian cancer, prostate cancer, and melanoma. In some embodiments, the disease or condition can be a tumor selected from the group consisting of lung tumor, breast tumor, colon tumor, ovarian tumor, prostate tumor, and melanoma tumor. In some embodiments, a polymer conjugate described herein can be administered intravenously.

As used herein, a "subject" refers to an animal that is the object of treatment, observation or experiment. "Animal" includes cold- and warm-blooded vertebrates and invertebrates such as fish, shellfish, reptiles and, in particular, mammals. "Mammal" includes, without limitation, mice, rats, rabbits, guinea pigs, dogs, cats, sheep, goats, cows, horses, primates, such as monkeys, chimpanzees, and apes, and, in particular, humans.

As used herein, the terms "treating," "treatment," "therapeutic," or "therapy" do not necessarily mean total cure or abolition of the disease or condition. Any alleviation of any undesired signs or symptoms of a disease or condition, to any extent can be considered treatment and/or therapy. Furthermore, treatment may include acts that may worsen the patient's overall feeling of well-being or appearance.

The term "effective amount" is used to indicate an amount of an active compound, or pharmaceutical agent, that elicits the biological or medicinal response indicated. For example, an effective amount of compound can be the amount needed to prevent, alleviate or ameliorate symptoms of disease or prolong the survival of the subject being treated This response may occur in a tissue, system, animal or human and includes alleviation of the signs or symptoms of the disease being treated. Determination of an effective amount is well within the capability of those skilled in the art, in view of the disclosure provided herein. The effective amount of the compounds disclosed herein required as a dose will depend on the route of administration, the type of animal, including human, being treated, and the physical characteristics of the specific animal under consideration. The dose can be tailored to achieve a desired effect, but will depend on such factors as weight, diet, concurrent medication and other factors which those skilled in the medical arts will recognize.

As will be readily apparent to one skilled in the art, the useful in vivo dosage to be administered and the particular mode of administration will vary depending upon the age, weight, the severity of the affliction, and mammalian species treated, the particular compounds employed, and the specific use for which these compounds are employed. The determination of effective dosage levels, that is the dosage levels necessary to achieve the desired result, can be accomplished by one skilled in the art using routine methods, for example, human clinical trials and in vitro studies.

The dosage may range broadly, depending upon the desired effects and the therapeutic indication. Alternatively dosages may be based and calculated upon the surface area of the patient, as understood by those of skill in the art. Although the exact dosage will be determined on a drug-by-drug basis, in most cases, some generalizations regarding the dosage can be made. The daily dosage regimen for an adult human patient may be, for example, an oral dose of between 0.01 mg and 3000 mg of each active ingredient, preferably between 1 mg and 700 mg, e.g. 5 to 200 mg. The dosage may be a single one or a series of two or more given in the course of one or more days, as is needed by the subject. In some embodiments, the compounds will be administered for a period of continuous therapy, for example for a week or more, or for months or years.

In instances where human dosages for compounds have been established for at least some condition, those same dosages may be used, or dosages that are between about 0.1% and 500%, more preferably between about 25% and 250% of the established human dosage. Where no human dosage is established, as will be the case for newly-discovered pharmaceutical compositions, a suitable human dosage can be inferred from $ED_{50}$ or $ID_{50}$ values, or other appropriate values derived from in vitro or in vivo studies, as qualified by toxicity studies and efficacy studies in animals.

In cases of administration of a pharmaceutically acceptable salt, dosages may be calculated as the free base. As will be understood by those of skill in the art, in certain situations it may be necessary to administer the compounds disclosed herein in amounts that exceed, or even far exceed, the above-stated, preferred dosage range in order to effectively and aggressively treat particularly aggressive diseases or infections.

Dosage amount and interval may be adjusted individually to provide plasma levels of the active moiety which are sufficient to maintain the modulating effects, or minimal effective concentration (MEC). The MEC will vary for each compound but can be estimated from in vitro data. Dosages necessary to achieve the MEC will depend on individual characteristics and route of administration. However, HPLC assays or bioassays can be used to determine plasma concentrations. Dosage intervals can also be determined using MEC value. Compositions should be administered using a regimen which maintains plasma levels above the MEC for 10-90% of the time, preferably between 30-90% and most preferably between 50-90%. In cases of local administration or selective uptake, the effective local concentration of the drug may not be related to plasma concentration.

It should be noted that the attending physician would know how to and when to terminate, interrupt, or adjust administration due to toxicity or organ dysfunctions. Conversely, the attending physician would also know to adjust treatment to higher levels if the clinical response were not adequate (precluding toxicity). The magnitude of an administered dose in the management of the disorder of interest will vary with the severity of the condition to be treated and to the route of administration. The severity of the condition may, for example, be evaluated, in part, by standard prognostic evaluation methods. Further, the dose and perhaps dose frequency, will also vary according to the age, body weight, and response of the individual patient. A program comparable to that discussed above may be used in veterinary medicine.

Compounds disclosed herein can be evaluated for efficacy and toxicity using known methods. For example, the toxicology of a particular compound, or of a subset of the compounds, sharing certain chemical moieties, may be established by determining in vitro toxicity towards a cell line, such as a mammalian, and preferably human, cell line. The results of such studies are often predictive of toxicity in animals, such as mammals, or more specifically, humans. Alternatively, the toxicity of particular compounds in an animal model, such as mice, rats, rabbits, or monkeys, may be determined using known methods. The efficacy of a particular compound may be established using several recognized methods, such as in vitro methods, animal models, or human clinical trials. When selecting a model to determine efficacy, the skilled artisan can be guided by the state of the art to choose an appropriate model, dose, route of administration and/or regime.

EXAMPLES

The following examples are provided for the purposes of further describing the embodiments described herein, and do not limit the scope of the claims.

Materials:

Poly-L-glutamate sodium salts with different molecular weights (average molecular weights of 41,400 (PGA(97 k)), 17,600 (PGA(44 k)), 16,000 (PGA(32 k)), and 10,900 (PGA (21 k)) daltons based on multi-angle light scattering (MALS)); 1,3-dicyclohexyl carbodiimide (DCC); N-(3-dimethylaminopropyl)-N'-ethylcarbodiimide hydrochloride (EDC); hydroxybenzotriazole (HOBt); pyridine; 4-dimethylaminopyridine (DMAP); N,N'-dimethylformamide (DMF); gadolinium-acetate; chloroform; and sodium bicarbonate were purchased from Sigma-Aldrich Chemical company. Poly-L-glutamate was converted into poly-L-glutamic acid using 2 N hydrochloric acid solution. Trifluoroacetic acid (TFA) was purchased from Bioscience. L-Aspartic acid β-t-butyl α-t-butyl ester hydrochloride (H-Asp(OtBu)-OtBu-.HCl), L-glutamic acid di-t-butyl ester hydrochloride (H-Glu (OtBu)-OtBu.HCl), N-α-CBZ-L-glutamic acid α-benzyl ester (Z-Glu-OBzl) were purchased from Novabiochem (La Jolla, Calif.). Paclitaxel was purchased from PolyMed (Houston, Tex.).

$^1$H NMR was obtained from Joel (400 MHz), and particle sizes were measured by ZetalPals (Brookhaven Instruments Corporation). Microwave chemistry was carried out in Biotage. Molecular weights of polymers were determined by size exclusion chromatography (SEC) combined with a multi-angle light scattering (MALS) (Wyatt Corporation) detector:

SEC-MALS Analysis Conditions:
HPLC system: Agilent 1200
Column: Shodex SB 806M HQ
(exclusion limit for Pullulan is 20,000,000, particle size: 13 micron, size (mm) ID×Length; 8.0×300)
Mobile Phase: 1×DPBS or 1% LiBr in DPBS (pH7.0)
Flow Rate: 1 ml/min
MALS detector: DAWN HELEOS from Wyatt
DRI detector: Optilab rEX from Wyatt
On-line Viscometer: Visco Star from Wyatt
Software: ASTRA 5.1.9 from Wyatt
Sample Concentration: 1-2 mg/ml
Injection volume: 100 μl
dn/dc value of polymer: 0.185 was used in the measurement.

BSA was used as a control before actual samples are run.

Using the system and conditions described above (hereinafter, referred to as the Heleos system with MALS detector), the average molecular weight of the starting polymers (poly-L-glutamate sodium salts average molecular weights of 41,400, 17,600, 16,000, and 10,900 daltons reported by Sigma-Aldrich using their system with MALS) were experimentally found to be 49,000, 19,800, 19,450, and 9,400 daltons, respectively.

The content of paclitaxel in the polymer-paclitaxel conjugates was estimated by UV/Vis spectrometry (Lambda Bio 40, PerkinElmer) based on a standard curve generated with known concentrations of paclitaxel in methanol ($\lambda$=228 nm).

Example 1

Synthesis of Polymer Conjugates

An example of a polymer conjugate incorporating Linker A and paclitaxel was synthesized using the following general, non-limiting steps:
i) N-Alkylation
ii) TBDPS protection.
iii) Deprotection of t-Bu group
iv) Synthesis of TBDPS-PEG-piperizine-acetic-PTX
v) TBDPS deprotection
vi) Synthesis of cPGGA-PEG-piperazine-glyco-PTX.

Figure 3:
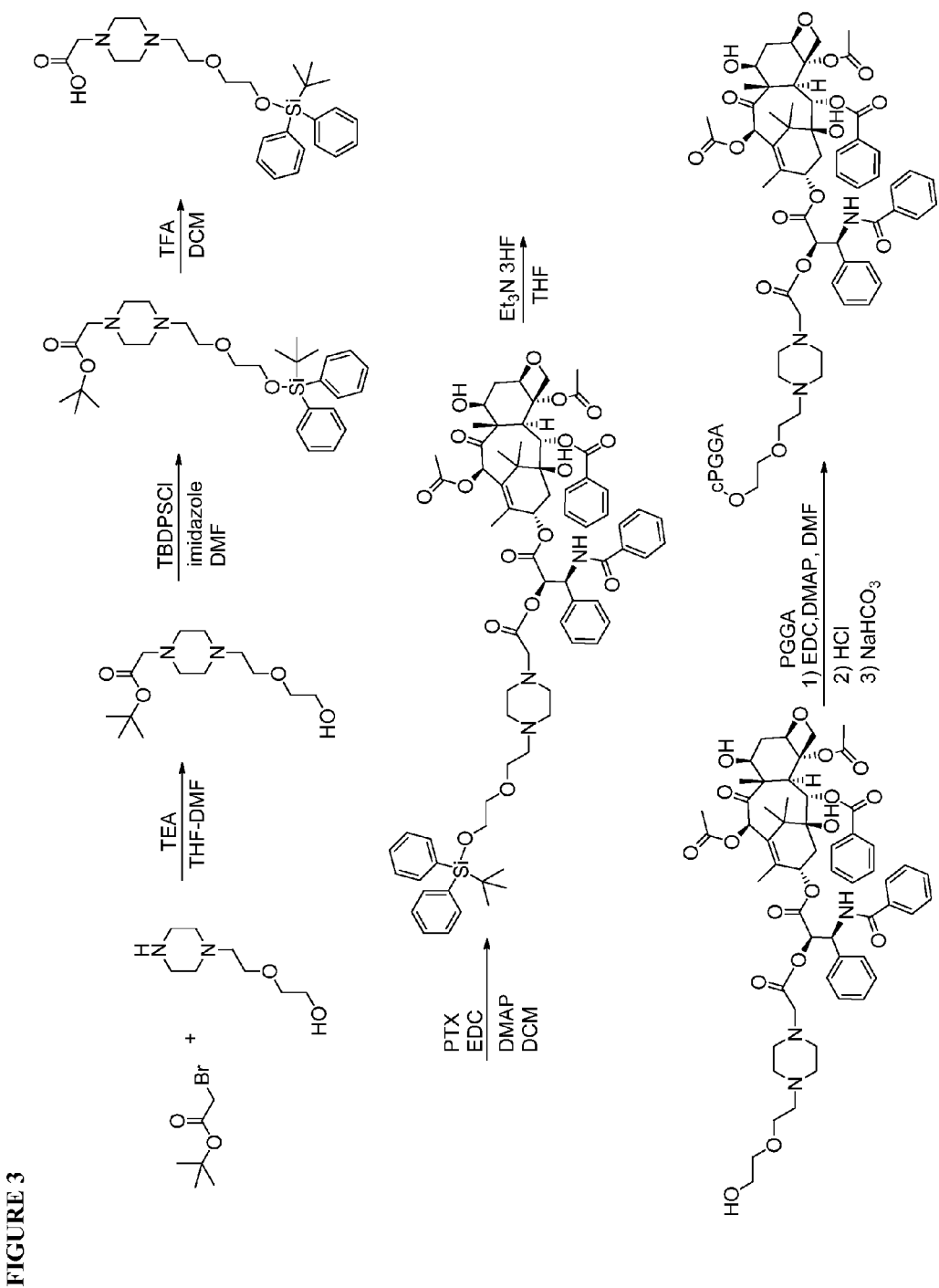
FIG. 3 illustrates a reaction scheme for the preparation of a poly(L-γ-glutamyl-glutamine)-Linker A-paclitaxel (PTX) conjugate, according to Example 1.

These steps are illustrated in FIG. 3, and described in further detail below.

i) N-alklation—Synthesis of tert-butyl 2-(4-(2-(2-hydroxyethoxy)ethyl)piperazin-1-yl)acetate 1-[2-(2-hydroxyethoxyl)ethyl]piperizine (12.36 g, 71.8 mmol) in tetrahydrofuran (THF) (60 mL) was added to bromoacetic acid tert-butyl ester (14.00 g, 71.8 mmol) in THF (10 mL). Triethanolamine (TEA) (22 mL, 143.5 mmol) was then added. DMF (30 mL) was added to the mixture to dissolve any solids. The reaction mixture was stirred at 50° C. for approximately 16 hours (overnight). NH$_4$Cl (20 g, 370 mmol) and water (20 mL) were added to the mixture. The organic layer was extracted with ethylacetate (EtOAc). The organic layers were combined, concentrated, and purified by silica gel column chromatography (5-10% methanol (MeOH) in ethylacetate) to give of the target product as an oil (16 g, 77% yield). $^1$H NMR (400 MHz, CDCl$_3$) (ppm) 3.70-3.55 (m, 7H), 3.09 (s, 2H), 2.52-2.80 (m, 10H), 1.44 (s, 9H).

ii). TBDPS Protection—Synthesis of tert-butyl 2-(4-(2-(2-tert-butyldiphenylsilyl)oxy)ethoxy)ethyl)piperazin-1-yl)acetate A solution of tert-butyl 2-(4-(2-(2-hydroxyethoxy)ethyl) piperazin-1-yl)acetate (16 g, 56 mmol) and imidazole (5.7 g, 83 mmol) in DMF (40 mL) was treated with t-butyl diphenylsilylchloride (TBDPSCl) (23 g, 83 mmol) in DMF (10 mL). The mixture was stirred at room temperature for approximately 16 hours. Water (100 mL) was added to the mixture. The mixture was extracted with EtOAc (3×100 mL). The combined organic layers were concentrated and purified by silica gel column chromatography (50% EtOAc in Hexane) to give the target product as an oil (24 g, 81% yield). $^1$H NMR (400 MHz, CDCl$_3$) (ppm) 7.58-7.68 (m, 4H), 7.36-7.48 (m, 6H), 3.78 (t, J=4.5 Hz, 2H), 3.55-3.65 (m, 4H), 3.55 (t, J=4.5 Hz, 2H), 3.08 (s, 2H), 2.40-2.70 (m, 8H), 1.45 (s, 9H), 1.03 (s, 9H).

iii). Deprotection of t-Bu Group—Synthesis of 2-(4-(2-(2-((tert-butyldiphenylsilyl)oxy)ethoxy)ethyl)piperazin-1-yl)acetic acid Tert-butyl-2-(4-(2-(2-((tert-butyldiphenylsilyl)oxy)ethoxy)ethyl)piperazin-1-yl)acetate (2.2 g, 4.18 mmol) was dissolved in dichloromethane (20 mL). Trifluoroacetic acid (TFA) (9.4 mL, 126 mmol) was added. The mixture was stirred at room temperature for approximately 5 hours. TFA and dichloromethane were co-evaporated with toluene 3 times by the addition of toluene each time. The crude product was purified by silica gel column chromatography (0-10% MeOH in dichloromethane) to give a pale yellow solid (1.29 g, 65% yield). $^1$H NMR (400 MHz, CDCl$_3$) (ppm) 7.61-7.68 (m, 4H), 7.35-7.44 (m, 6H), 3.85-3.77 (m, 4H), 3.35-3.55 (m, 8H), 3.10-3.24 (m, 6H), 1.02 (s, 9H).

iv). TBDPS-PEG-piperizine-acetic-PTX—Synthesis of (2aR,4S,4aS,6R,9S,11S,12S,12aR,12bS)-9-(((2R,3S)-3-benzamido-2-(2-(4-(2-(2-((tert-butyldiphenylsilyl)oxy)ethoxy)ethyl)piperazin-1-yl)acetoxy)-3-phenylpropanoyl)oxy)-12-(benzoyloxy)-4,11-dihydroxy-4a,8,13,13-tetramethyl-5-oxo-2a,3,4,4a,5,6,9,10,11,12,12a,12b-dodecahydro-1H-7,11-methanocyclodeca[3,4]benzo[1,2-b]oxete-6,12b-diyl diacetate To a solution of 2-(4-(2-(2-((tert-butyldiphenylsilyl)oxy)ethoxy)ethyl)piperazin-1-yl)acetic acid (1290 mg, 2.74 mmol) in dichloromethane (20 mL) in a round bottom flask with a stir bar at 0° C. were added paclitaxel (1637 mg, 1.92 mmol), N1-((ethylimino)methylene)-N3,N3-dimethylpropane-1,3-diamine hydrochloride (EDC) (789 mg, 4.11 mmol), (4-Dimethylamino)pyridine (DMAP) (33 mg, 0.274 mmol) and Diisopropylethylamine (DIPEA) (2.38 mL, 13.7 mmol). The reaction mixture was stirred at 0° C. for approximately 2 hours, warmed to room temperature and stirred for approximately 16 hours at room temperature under argon atmosphere. The reaction mixture was purified by silica gel column chromatography (80-100% of EtOAc in Hexane) to give a white solid (800 mg, 32% yield). $^1$H NMR (400 MHz, CDCl$_3$) (ppm) 8.12-8.17 (m, 2H), 7.72-7.77 (m, 2H), 7.66-7.68 (m, 4H), 7.58-7.62 (m, 1H), 7.45-7.54 (m, 3H), 7.30-7.45 (m, 13H), 7.08-7.13 (m, 1H), 6.22-6.32 (m, 2H), 5.98-6.01 (m, 1H), 5.60-5.70 (m, 1H), 5.53-5.55 (m, 1H), 4.96-4.99 (m, 1H), 4.41-4.50 (m, 1H), 4.31 (d, J=8.8 Hz, 1H), 4.19 (d, J=8.8 Hz, 1H), 4.07-4.15 (m, 1H), 3.76-3.82 (m, 4H), 3.52-3.65 (m, 5H), 3.20-3.33 (m, 2H), 2.46-2.57 (m, 14H), 2.22 (s, 3H), 1.93 (s, 3H), 1.79-1.90 (m, 2H), 1.67 (s, 3H), 1.22 (s, 3H), 1.12 (s, 3H), 1.03 (s, 9H). LCMS, M+1: 1306.8.

v). TBDPS Deprotection—Synthesis of (2aR,4S,4aS,6R,9S,11S,12S,12aR,12bS)-9-(((2R,3S)-3-benzamido-2-(2-(4-(2-(2-hydroxyethoxy)ethyl)piperazin-1-yl)acetoxy)-3-phenylpropanoyl)oxy)-12-(benzoyloxy)-4,11-dihydroxy-4a,8,13,13-tetramethyl-5-oxo-2a,3,4,4a,5,6,9,10,11,12,12a,12b-dodecahydro-1H-7,11-methanocyclodeca[3,4]benzo[1,2-b]oxete-6,12b-diyl diacetate To a solution of TBDPS-PEG-piperizine-acetic-PTX from step (iv) (500 mg, 0.33 mmol) in THF (10 mL), was added Et$_3$N-3HF (0.54 mL) at 0° C. The mixture was warmed to room temperature and stirred for approximately 18 hours. TLC showed the main single product. The reaction mixture was purified by silica gel column chromatography (5-10% MeOH in DCM) to give the product as a white solid (330 mg, 94% yield). $^1$H NMR (400 MHz, CDCl$_3$) (ppm) 8.14 (d, J=7.4 Hz, 2H), 7.75 (d, J=7.4 Hz, 2H), 7.58-7.68 (m, 2H), 7.45-7.56 (m, 4H), 7.25-7.40 (m, 6H), 6.20-6.28 (m, 2H), 6.01-6.04 (m, 1H), 5.67 (d, J=5.7.3 Hz, 1H), 5.58 (d, J=3.3 Hz, 1H), 4.95-4.98 (m, 1H), 4.41-4.49 (m, 1H), 4.31 (d, J=8.0 Hz, 1H), 4.19 (d, J=8.0 Hz, 1H), 3.80 (d, J=7.32 Hz, 1H), 3.47-3.63 (m, 9H), 3.35 (d, J=3.3 Hz, 2H), 2.46-2.60 (m, 5H), 2.46 (s, 3H), 2.31-2.40 (m, 2H), 2.22 (s, 3H), 2.07-2.15 (m, 2H), 1.93 (s, 3H), 1.84-1.95 (m, 2H), 1.69-1.80 (m, 2H), 1.67 (s, 3H), 1.21 (s, 3H), 1.17 (s, 3H). LCMS, M+1: 1068.8.

vi). Synthesis of cPGGA-PEG-piperazine-co-PTX

To an oven dried 250 mL round bottom flask with a magnetic stir bar cooled under argon were added c-PGGA (1420 mg) and DMF (20 mL). The solution was stirred at room temperature for 10 min. N1-((ethylimino)methylene)-N3,N3-dimethylpropane-1,3-diamine hydrochloride (EDC) (1374 mg, 7.15 mmol) was added, and the mixture stirred for 15 min. TBDPS-deprotected alcohol, the compound from step (v) (470 mg, 0.44 mmol) in DMF (30 mL) was added, followed by the addition of DMAP (202 mg, 1.65 mmol). The mixture was stirred at room temperature for approximately 20 hours. The mixture was then diluted with water (150 mL), and a suspension was transferred to tubing. The pH was adjusted to about 2.97 using 1N HCl. The suspension was then subjected to dialysis for 24 hours, during which the dialysis water was changed 8 times. The pH was adjusted to 7.01 using a 1N NaHCO$_3$ aqueous solution. The mixture was subjected to dialysis, during which the dialysis water was changed 8 times. The solution was then frozen, and the dry material was obtained through lyophilization. The lyophilized material was dissolved in water. The solution was then purified using Tangential Flow Filtration (TFF) under acidic conditions followed by basic conditions. The solution was then frozen and dried through lyophilization. The product was obtained as a white powder (1.6 g, 85% yield).

Example 2

Release Studies

LC-MS instrument, methodology, and standards.
LC-MS Instrument (Agilent LC 1100, MS G1956B)
Column (Agilent Eclipse XDB C18, 5 μm, 150×4.6 mm, SN # B07016)
Solvent A: Milli Q water with 0.1% formic acid
Solvent B: LC-MS grade acetonitrile with 0.1% formic acid
Flow rate: 0.8 mL/min
Detection wavelength: 230 nm
Column temperature: 25° C.
Sample chamber temperature: 4° C.

|  | Time** (mins) | % A | % B |
|---|---|---|---|
| Gradient: | 0 | 80 | 20 |
|  | 15 | 5 | 95 |
|  | 20 | 5 | 95 |

-continued

| Time** (mins) | % A | % B |
|---|---|---|
| 21 | 80 | 20 |
| 24 | 80 | 20 |

MS detection mode: positive; Range: 70-200

The paclitaxel standard in methanol was run once after every sample set to make sure the system suitability was valid, which was defined as % RSD≤2%.

Analysis of the drug release of the polymer paclitaxel conjugates was performed using the following LC-MS method. A solution of the polymer paclitaxel conjugates (0.36 mg/mL as paclitaxel equivalent) was dissolved in 1 mL of 20% human plasma-PBS. The sample vials were placed in an incubator at 37° C. with continuous agitation. In a pre-defined time interval (4, 8, 24, 48, 72 & 96 hrs), two vials of each sample plus a control were withdrawn from the incubator and extracted with 2×2 mL of ethyl acetate (EtOAc) as follows. The EtOAc was removed by SpeedVac. The residue was reconstituted with 1 mL of methanol and filtered through a 0.2 μm syringe filter, and sent for LC-MS analysis. Results are shown in FIG. 4.

Figure 4:
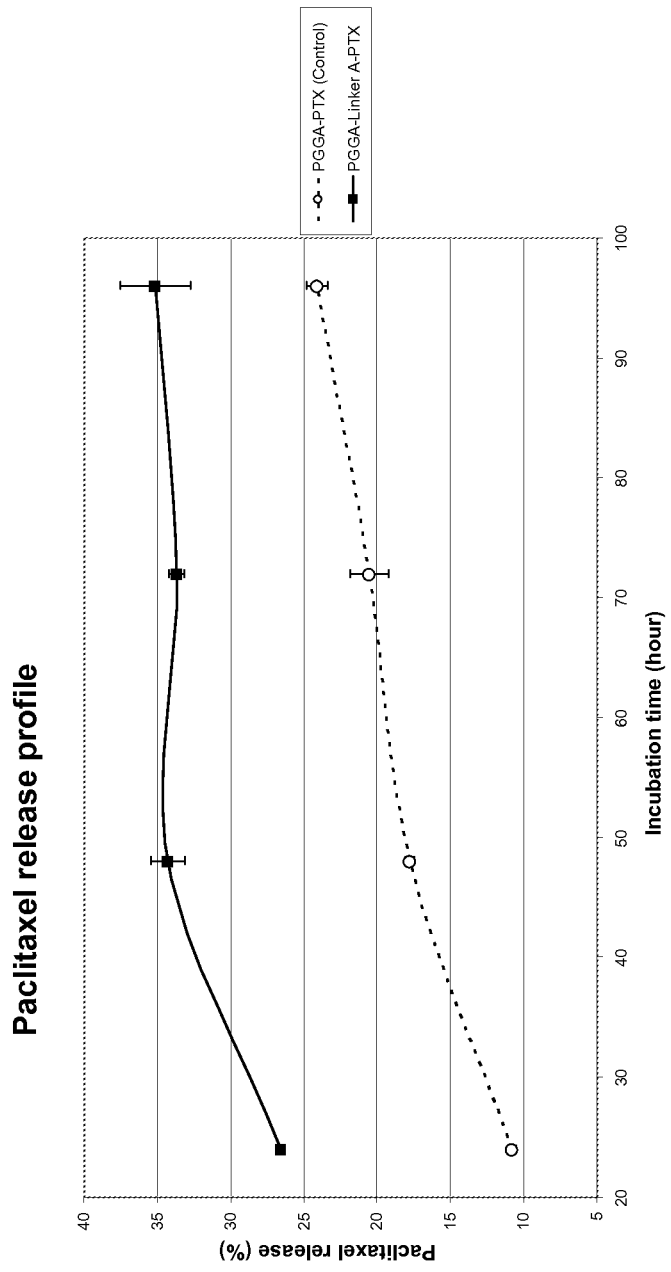
FIG. 4 shows a plot that illustrates the release of paclitaxel from a poly(L-γ-glutamyl-glutamine)-Linker A-PTX conjugates compared to a poly(L-γ-glutamyl-glutamine)-PTX conjugates in 20% human plasma-phosphate buffered saline (PBS) at 37° C.

The results in FIG. 4 show the rate of paclitaxel release over time. FIG. 4 illustrates that a polymer conjugate that includes a recurring unit of Formula (I) that includes Linker A and a recurring unit of Formula (II) release a greater amount of PTX compared to the poly(L-γ-glutamyl-glutamine)-PTX control over several hours.

Example 3

In Vivo Assay

Establishment of NCI-H460 Tumor Xenograft

NCI-H460 cell line was purchased from ATCC and maintained in RPMI-1640 supplemented with 10% Fetal Bovine Serum, 100 U/ml penicillin and 100 μg/ml streptomycin. Cells were in log phase growth when harvested. The cells were lightly trypsinized with trypsin-EDTA and harvested from the tissue culture. The number of viable cells were counted and determined in a hemocytometer in the presence of trypan blue (only viable cells are counted). Each mouse was inoculated subcutaneously in the right flank with 0.1 mL of an inoculum of 3×10$^6$ of NCI-H460 cells using a 25 G needle and syringe. (one inoculum per mouse). Tumor volume was monitored twice a week. Bodyweight measurements were also taken. Tumor volume was calculated using the formula: Tumor volume=(length×(width))/2.

Efficacy of Test Articles

Once the established tumors reached approximately 75-125 mm$^3$ (average tumor volume at 100 mm$^3$), the mice were assigned into the vehicle control and various treatment groups, such that the mean tumor volumes in the treated groups were within 10% of the mean tumor volume in the vehicle control group, and the CV % of tumor volume was less than 25%. On the same day, freshly prepared test articles and the vehicle control group were injected through a tail vein at dosages of 175 and 250 mg (PTX equiv.)/kg, and a dosing volume of 10 mL/kg. Tumor volume was monitored twice a week. Bodyweight measurements were also taken. Tumor volume was calculated using the formula provided above: The individual tumor volume reached 3,000 mm$^3$ or the tumor ulcerated, and the animals were sacrificed based on IACUC regulations.

Body Weight Measurement

Bodyweights were monitored and recorded daily for the first week starting on the first day of treatment and twice a week after the first week, including the day of study termination.

Dosing Solution Preparation

Dosing solutions were prepared freshly on the day of administration. Test articles were dissolved in PBS (pH 7.4) at a concentration PTX equivalent/mL to meet the dosage and dosing volume of 10 mL per kilogram. Abraxane (clinical grade) was diluted in saline at a concentration of 8 mg/mL (PTX equivalent).

Figure 5:
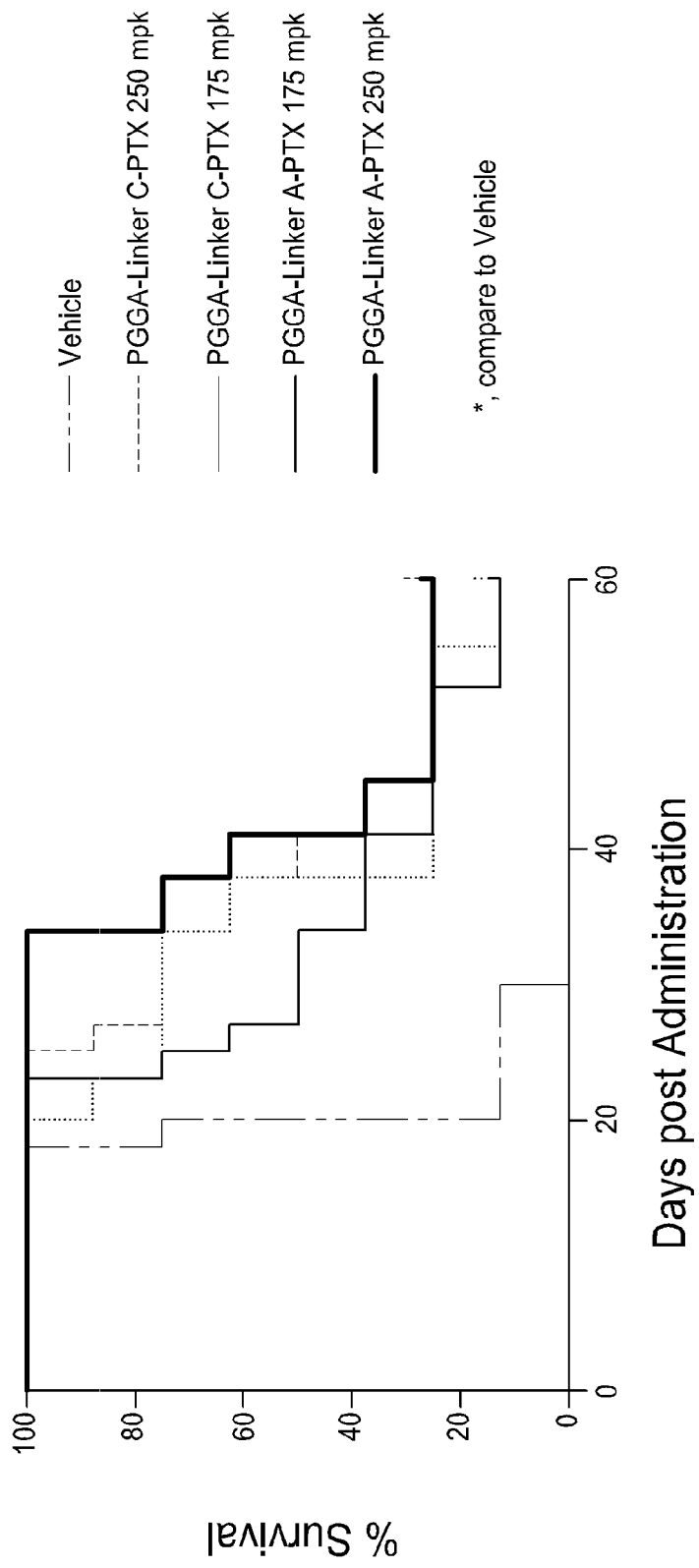
FIG. 5 shows a plot that illustrates the percent survival of the test animals after being injected with a poly(L-γ-glutamyl-glutamine)-Linker A-PTX conjugate, a poly(L-γ-glutamyl-glutamine)-Linker C-PTX conjugate or the vehicle control.
Figure 6:
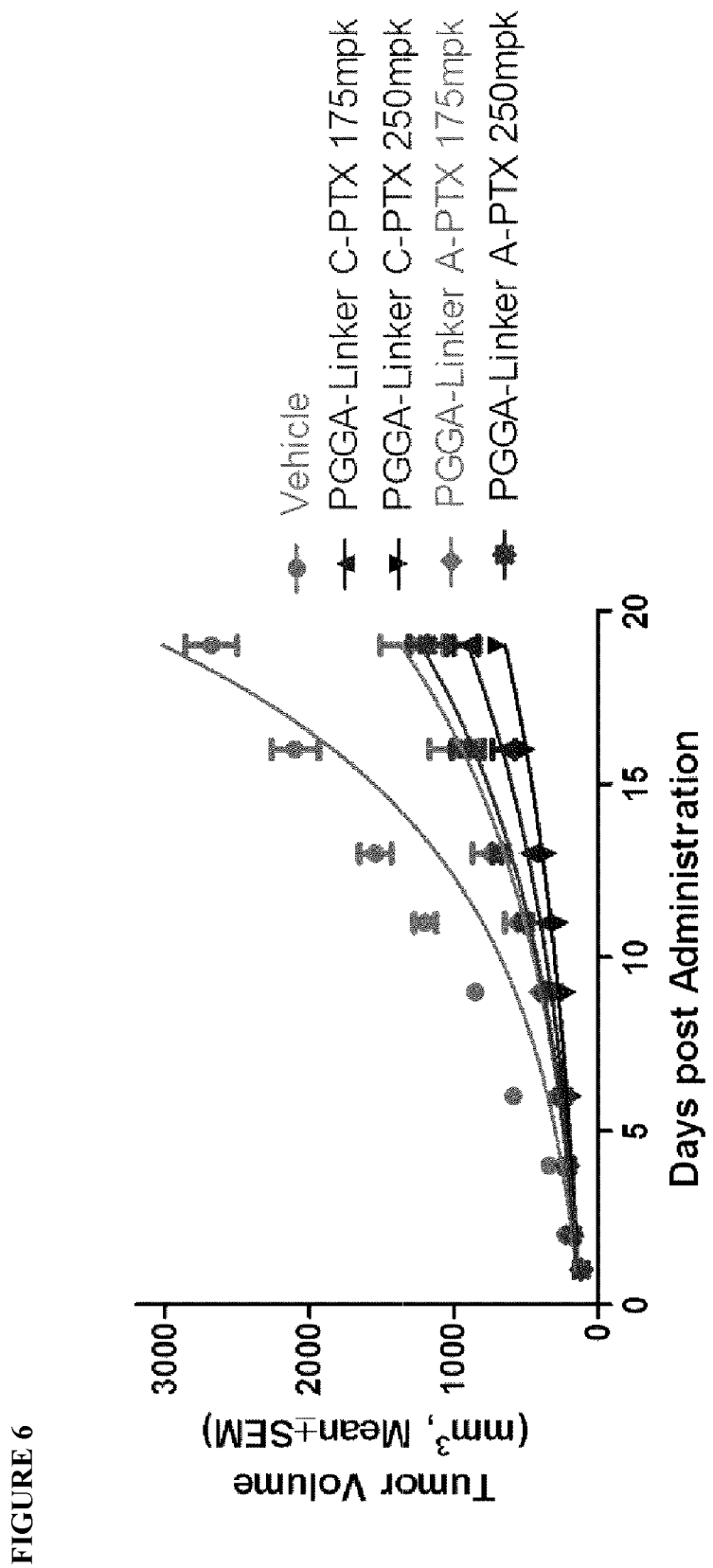
FIG. 6 shows a plot that illustrates the tumor volume over several days following administration of a poly(L-γ-glutamyl-glutamine)-Linker A-PTX conjugate, a poly(L-γ-glutamyl-glutamine)-Linker C-PTX conjugate or the vehicle control.

The results are shown in FIGS. 5 and 6. FIG. 5 illustrates that mice injected with a polymer conjugate that includes a recurring unit of Formula (I), a recurring unit of Formula (II) and a linker as described herein compared to the vehicle control survive longer. FIG. 6 shows that polymer conjugate with a linker described herein reduces the tumor volume to a greater degree than the vehicle control.

Furthermore, although the foregoing has been described in some detail by way of illustrations and examples for purposes of clarity and understanding, it will be understood by those of skill in the art that numerous and various modifications can be made without departing from the spirit of the present disclosure. Therefore, it should be clearly understood that the forms disclosed herein are illustrative only and are not intended to limit the scope of the present disclosure, but rather to also cover all modification and alternatives coming with the true scope and spirit of the invention.

What is claimed is:

1. A polymer conjugate comprising a recurring unit of the Formula (I) and a recurring unit of the Formula (II):

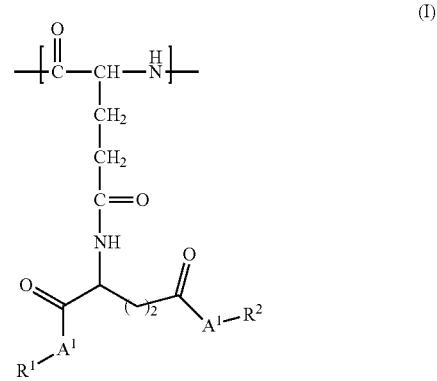

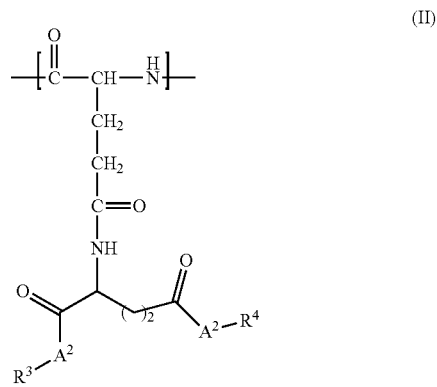

wherein:

each $A^1$ and each $A^2$ are independently oxygen or $NR^5$, wherein $R^5$ is hydrogen or $C_{1-4}$ alkyl;

each $R^1$ and each $R^2$ are independently selected from the group consisting of hydrogen, a $C_{1-10}$ alkyl group, a $C_{6-20}$ aryl group, ammonium, an alkali metal, and a compound that comprises a linker and an anticancer drug, provided that at least one of $R^1$ and $R^2$ is a compound that comprises a linker and an anticancer drug; wherein the linker has the structure:

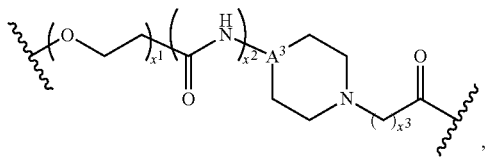

wherein $A^3$ is N or CH; $X^1$ is 1, 2, 3, 4, 5 or 6; $X^2$ is 0 or 1; and $X^3$ is 1, 2 or 3; and each $R^3$ and each $R^4$ are independently selected from the group consisting of hydrogen, a $C_{1-10}$ alkyl group, a $C_{6-20}$ aryl group, ammonium, and an alkali metal.

2. The polymer conjugate of claim 1, wherein $X^1$ is 2, $X^2$ is 0, $A^3$ is N, and $X^3$ is 1.

3. The polymer conjugate of claim 1, wherein $X^1$ is 2, $X^2$ is 0, $A^3$ is N, and $X^3$ is 2.

4. The polymer conjugate of claim 1, wherein $X^1$ is 4, $X^2$ is 1, $A^3$ is CH, and $X^3$ is 1.

5. The polymer conjugate of claim 1, wherein the anticancer drug is selected from the group consisting of a taxane, camptotheca and an anthracycline.

6. The polymer conjugate of claim 5, wherein the taxane is selected from the group consisting of paclitaxel and docetaxel.

7. The polymer conjugate of claim 5, wherein the taxane is paclitaxel.

8. The polymer conjugate of claim 5, wherein the camptotheca is camptothecin.

9. The polymer conjugate of claim 5, wherein the anthracycline is doxorubicin.

10. The polymer conjugate of claim 1, wherein the polymer conjugate comprises an amount of the anticancer drug in the range of about 5% to about 40% (weight/weight) based on the mass ratio of the anticancer drug to the polymer conjugate.

11. The polymer conjugate of claim 1, wherein the polymer conjugate comprises an amount of the anticancer drug in the range of about 10% to about 30% (weight/weight) based on the mass ratio of the anticancer drug to the polymer conjugate.

12. The polymer conjugate of claim 1, wherein the other one of $R^1$ and $R^2$ is an alkali metal, each $R^3$ and each $R^4$ is an alkali metal.

13. The polymer conjugate of claim 1, wherein the other one of $R^1$ and $R^2$ is hydrogen, and each $R^3$ and each $R^4$ is hydrogen.

14. The polymer conjugate of claim 1, wherein each $A^1$ and each $A^2$ is oxygen.

15. The polymer conjugate of claim 1, wherein the polymer conjugate releases at least about 5% more of the anticancer drug compared to a comparable poly(L-γ-glutamyl-glutamine)-(anticancer drug) conjugate that comprises substantially the same amount of the anticancer drug.

16. A pharmaceutical composition comprising one or more compounds of claim 1, and at least one selected from a pharmaceutically acceptable excipient, a carrier, and a diluent.

17. A method for treating or ameliorating a disease or condition comprising administering an effective amount of the polymer conjugate of claim 1 to a mammal in need thereof.

18. The method of claim 17, wherein the disease or condition is selected from the group consisting of lung cancer, breast cancer, colon cancer, ovarian cancer, prostate cancer and melanoma.

19. The method of claim 17, wherein the polymer conjugate is in the form of an injectable liquid.

* * * * *